(12) United States Patent
van Groeninghen

(10) Patent No.: US 7,695,722 B2
(45) Date of Patent: Apr. 13, 2010

(54) METHODS FOR REDUCING GNRH-POSITIVE TUMOR CELL REPLICATION

(76) Inventor: Johannes C. van Groeninghen, Karlsbank 9A, 44229, Dortmund (DE)

(*) Notice: Subject to any disclaimer, the term of this patent is extended or adjusted under 35 U.S.C. 154(b) by 0 days.

(21) Appl. No.: 10/327,621

(22) Filed: Dec. 20, 2002

(65) Prior Publication Data

US 2003/0166503 A1 Sep. 4, 2003

Related U.S. Application Data

(63) Continuation-in-part of application No. 09/446,996, filed as application No. PCT/DE98/01902 on Jul. 3, 1998, now abandoned.

(30) Foreign Application Priority Data

Jul. 4, 1997 (DE) ................................ 197 28 737

(51) Int. Cl.
- A61K 38/16 (2006.01)
- A61K 38/00 (2006.01)
- G01N 33/53 (2006.01)

(52) U.S. Cl. .................. 424/198.1; 514/2; 424/195.11; 435/7.1

(58) Field of Classification Search .............. 530/313; 435/69.4; 514/2
See application file for complete search history.

(56) References Cited

U.S. PATENT DOCUMENTS

| | | | |
|---|---|---|---|
| 5,633,274 A * | 5/1997 | Halperin et al. | 514/405 |
| 5,672,592 A * | 9/1997 | Jackson et al. | 514/75 |
| 5,760,000 A | 6/1998 | Habibi | |
| 5,985,834 A | 11/1999 | Engel | |
| 6,096,757 A * | 8/2000 | Bishop et al. | 514/290 |
| 6,140,066 A | 10/2000 | Lorberboum-Galski et al. | |
| 6,214,969 B1 * | 4/2001 | Janaky et al. | 530/313 |
| 6,242,421 B1 | 6/2001 | Bowen | |
| 6,933,271 B2 | 8/2005 | Yarkoni et al. | |

FOREIGN PATENT DOCUMENTS

| WO | WO 90/09799 | 7/1990 |
|---|---|---|
| WO | WO 90 09799 | 9/1990 |

OTHER PUBLICATIONS

Johnson et al. British J. Cancer, 2001, vol. 84(1), pp. 1424-1431.*
Laue et al. Amer. J. of Diseases of Children, 1985, vol. 139, No. 11, pp. 1097-1100.*
Nechushtan A. et al., Apr. 25, 1997, J. Biol. Chem., vol. 272, No. 17, pp. 11597-11603.*
He Y. J. et al., 1986, Clinical Chemistry, vol. 32, No. 6, pp. 1159, abstract #542.*
Laue L. et al., Nov. 1985, Amer. J. of Diseases of Children, vol. 139, No. 11, pp. 1097-1100.*
Kawai and Clark, 1986, Endocr. Res., 12(3):195-209. (Abstract).*
Dondi et al., Cancer Res., 1994, vol. 54:4091-4095.*
Noordzij et al., Urol. Res., 1995, vol. 22;333-341.*
Emons et al., Hum. Reprod., 1994, vol. 9(7):1364-1379.*
Van Groeninghen et al., Effects of luteinising-hormone-releasing hormone on nervous-system tumours, The Lancet, Aug. 1, 1998, pp. 372-373, vol. 352, No. 9125.
Moretti et al., Locally Expressed LHRH Receptors Mediate the Oncostatic and Antimetastatic Activity of LHRH Agonists on Melanoma Cells, J. of Clin, Endocrin. & Metab., 2002, pp. 3791-3797, vol. 87, No. 8.
Moretti et al., Inhibitory activity of luteinizing hormone-releasing hormone on tumor growth and progression, Endocrine-Related Cancer, 2003, pp. 161-167, vol. 10, No. 2.
Limonta et al., The biology of gonadotropin hormone-releasing hormone: role in the control of tumor growth and progression in humans, Front. Neuroendocrinol., 2003, pp. 279-295, vol. 24.
Hoitink et al., Stability of Gonadorelin and Relation Compounds, dissertation, U. of Utrecht, Aug. 6, 1998, Christopher Haughton. 1, p. 15, para. 2.
Rote Liste, 1997.
Mather, J.P. and Sato, G.H. Experimental Cell Research 120 (1979) 191-200.
Declaration of Loberboum-Glaski dated Jun. 11, 2003, in support of U.S. Appl. No. 09/147,346, issued as U.S. Patent No. 6,933,271 B2.
Keller et al., Human Malignant Melanomas Express Receptors for Luteinizing Hormone Releasing Hormone Allowing Targeted Therapy with Bytotoxic Luteinizing Hormone Releasing Hormone Analogue, Cancer Research, Jul. 1, 2005, pp. 5857-5863, vol. 65, No. 13.
Norwood Immunology—Phase II Clinical Trial—Melanoma Cancer Vaccine (Nov. 17, 2005) <http://biz.yahoo.com/bw/051117/20051117005541.html?.v=1>.
MDACC Study Summary No. 2004-0502 (Jan. 9, 2006) <http://utm-ext01a.mdacc.tmc.edu/dept/prot/clinicaltrialswp.nsf/Index/2004-0502>.
Van Groeninghen et al., Effects of luteinising-hormone-releasing hormone on nervous-system tumours, The Lancet, Aug. 1, 1998, pp. 372-373, vol. 352, No. 9125.
Moretti et al., Locally Expressed LHRH Receptors Mediate the Oncostatic and Antimetastatic Activity of LHRH Agonists on Melanoma Cells, J. Clin. Endocrinol. Metab. 2002, 87 (8) :3791-7.
Moretti et al., Inhibitory activity of luteinizing hormone-releasing hormone on tumor growth and progression, Endocrine-Related Cancer, (2003) 10(2) :161-7.
Limonta et al., The biology of gonadotropin hormone-releasing hormone: role in the control of tumor growth and progression in humans, Front. Neuroendocrinol., 2003, 24:279-295.

(Continued)

Primary Examiner—Gary B Nickol
Assistant Examiner—Xiaozhen Xie
(74) Attorney, Agent, or Firm—Stacey J. Farmer; Grund IP Group

(57) ABSTRACT

A method for recognizing and determining GnRH receptors on abnormal cells of a tumor originating in the brain and/or nervous system and/or the meninges and/or on Kaposi sarcoma. Also, preparing diagnostic kits for tumors originating in the brain and/or nervous system and/or the meninges and/or for Kaposi sarcoma. Further, a method for decreasing cellular replication of GnRH-positive glioma, oat-cell carcinoma, malignant melanoma, or Kaposi sarcoma comprising administering to a cell or to a subject a replication decreasing amount of a GnRH agonist.

6 Claims, 14 Drawing Sheets

OTHER PUBLICATIONS

Alexander et al., "Gonadotropin-releasing Hormone Receptor mRNA Expression by Human Pituitary Tumors In Vitro," J. Clin. Invest., 93: 2332-2339, Jun. 1994.

Karande et al., "Establishment of immunological probes to study human gonadotropin-releasing hormone receptors," ScienceDirect—Molecular and Cellular Endocrinology (Abstract only)(Nov, 16, 1999).

Abstract No. XP-002090711 (Biological Abstracts. Abstract No. PREV199497360906).

Abstract No. XP-002090712 (Chemical Abstracts. vol. 124. No. 23 (1996)).

Ackerman et al., Cancer Lett. 81(2):177-184 (1994) (Abstract Only).

Badr et al., Synapse 1(6):567-571 (1987) (Abstract Only).

Karande et al., Mol. Cell Endocrinol., 114(1-2): 51-56 (1995) (Abstract Only).

Leung et al., Biol. Signals, 5:63-69 (1996).

Compagni et al., British J. Cancer 2000. vol. 83, pp. 1-5.

Johnson et al., Brit. J. Cancer, 2001, vol. 84, pp. 1424-1431.

Shi et al., J. Chem. Inf. Comput. Sci., 2000, vol. 40, pp. 367-379.

* cited by examiner

Figure 1 Antide

Figure 2 triptorelin

Figure 3 LHRH Hormone

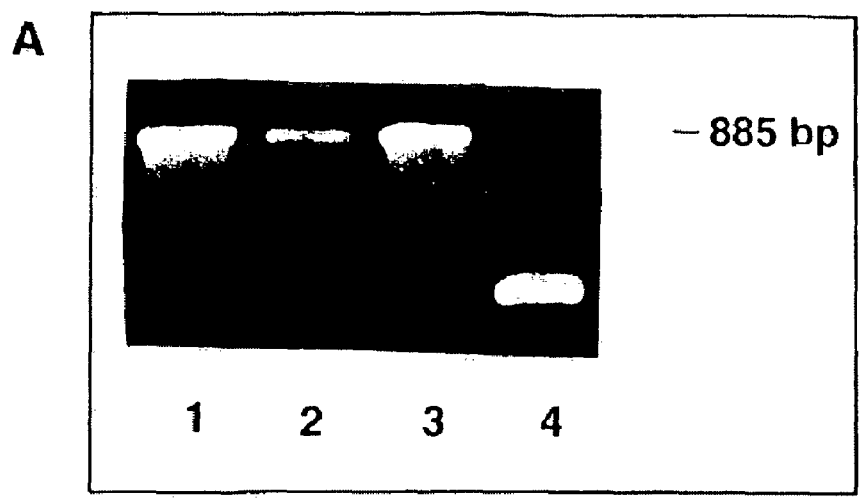
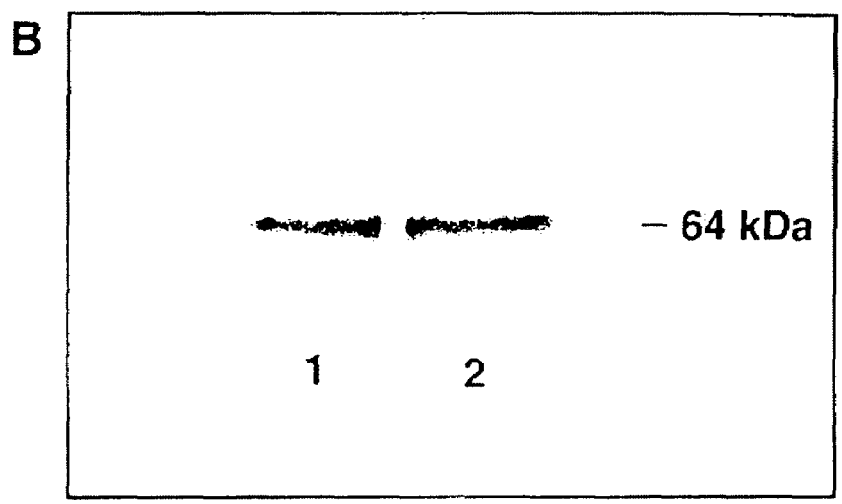
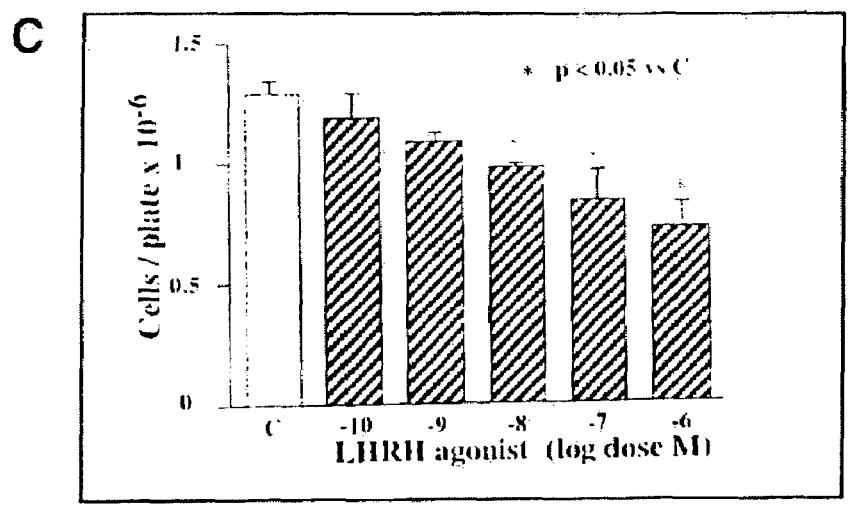
FIG. 12

METHODS FOR REDUCING GNRH-POSITIVE TUMOR CELL REPLICATION

CROSS-REFERENCE TO RELATED APPLICATION

This application is a continuation in part of U.S. application Ser. No. 09/446,996, filed on Dec. 30, 1999 now abandoned, the contents of which are incorporated by this reference, which was a national phase entry under 35 U.S.C. § 371 of International Patent Application PCT/DE98/01902, filed Jul. 3, 1998, published as International Patent Publication WO99/01764 on Jan. 14, 1999.

BACKGROUND OF THE INVENTION

1. Field of the Invention

The present invention relates to tumor diagnosis and therapy. In particular, it is directed to the diagnosis and therapy of tumors carrying GnRH receptors.

2. State of the Art

Post-operative treatment of prostate and mammary carcinomas with agonists of gonadotropin releasing hormone (GnRH, in the literature also referred to as luteinizing hormone releasing hormone; LH-RH) is a standard treatment; cf. Gonzalez-Barcena et al., 1994, The Prostate 24, 84-92; Emons and Schally, 1994, Human Reproduction Update 9, No. 7, 1364-1379. The GnRH receptor is a well-known target in tumor therapy.

Thus, in various steroid hormone (sexual hormone) dependent malignant tumors, such as mammary carcinoma, prostate carcinoma, ovarian carcinoma, and endometrial carcinoma, a double effect has been observed in clinical studies upon treatment with GnRH agonists:

1) an indirect anti-proliferative activity by uncoupling of the positive endocrine (estrogenous or androgenous) effect on tumor growth;

2) a direct anti-proliferative activity by an unknown mechanism via GnRH receptors in the tumor tissue itself; cf. Emons and Schally, 1994, Human Reproduction Update 9, 1364-1379.

This indirect effect due to steroid hormone dependence has been known for decades for the prostate and the mammary carcinoma; cf. Gonzalez-Barcena et al., 1994, The Prostate 24, 84-92; Jonat et al., 1995, European Journal of Cancer 31A, 137-142.

The direct anti-proliferative effect of GnRH agonists and GnRH antagonists on e.g. prostate carcinomas, mammary carcinomas, and ovarian carcinomas has been confirmed by clinical studies. Some of the GnRH agonists employed in these treatments having a direct anti-proliferative effect are known by the following trademarks of the medicaments approved in Germany: for example ZOLADEX®, ZOLADEX 10.8®, ZOLADEX GYN®, PROFACT®-DEPOT, PROFACT® PRO INJECTIONE/NASAL, SYNARELA®, ENANTONE MONATS-DEPOT®, UNO-ENANTONE®, ENANTONE GYN MONATS-DEPOT®, TRENANTONE®, SUPRECUR®, CARCINIL®, or DECAPEPTYL® 0.5 mg/0.1 mg, DECAPEPTYL® DEPOT, DECAPEPTYL® GYN as well as DECAPEPTYL® DIAGNOSTIK.

Research with cell culture has revealed that GnRH receptors are present on human primary liver cell carcinomas and pancreas adenocarcinomas. In addition, the beginning of a biochemical metabolization with respect to cleavage of GnRH between tyrosine 5 and glycine 6 in rat glioma and rat neuroblastoma has been described; cf. Tao et al., 1991, Neuropeptides 20, 125-131. Ligand binding of GnRH to the GnRH receptor and its signal transduction, however, takes place in a different way, namely at the eighth amino acid of GnRH, arginine, and this exclusively occurs in the case of an intact conformation of the GnRH molecule and its amino acid side chains (Naor, Z., Schacham, Sh., Harris, D., Seger, R., and Reiss, N., 1995, Signal Transduction of the Gonadotropin Releasing Hormone (GnRH) Receptor: Cross-Talk of Calcium, Protein Kinase C (PKC), and Arachidonic Acid. Cellular and Molecular Neurobiology, vol. 15, 527-545). In normal rat adenohypophysis where GnRH receptors reside, GnRH leads to an increased cAMP production, however, it is still unclear whether this is a direct or an indirect effect (paracrine interaction). For the function of the GnRH receptor in rat including secretion of LH as well as an increased production of LH stimulated by GnRH, the biochemical metabolization of GnRH, e.g. by means of cAMP, plays only an indirect role (Abdilnour, G., and Bourne, G. A., 1995, Adenosine 3',5'-cyclic mono-phosphate and the self-priming effect of gonadotropin-releasing hormone. Molecular and Cellular Endocrinology, 107, 1-7). Naturally, there were found GnRH receptors on human gonadotropin producing pituitary adenomas (Alexander, J. P., and Klibanski, A., Gonadotropin-releasing Hormone Receptor mRNA Expression by Human Pituitary Tumors In Vitro, 1994, Journal of Clinical Investigation, 93, 2332-2339).

In the case of glioma and other malignant tumors of ectodermal origin, such as malignant melanoma and in particular in the case of diffusely growing tumors in the nervous system or in the case of metastases (formation of disseminations, for example, in other organs such as oat-cell carcinoma in the lung) life expectancy is not optimistic. The same is true for Kaposi sarcoma. "Glioma" refers to mainly brain-localized true tumors of the central nervous system (CNS) originating in the neuroglia, i.e. from the covering and supporting tissue of the nervous system which is derived from ectoderm. These gliomas are present in various differentiation stages. Subtypes of glioma are spongioblastoma, oligodendroglioma, astrocytoma, glioblastoma, and retinoblastoma. In particular, the Glioblastoma multiforme (GBM) type of brain tumors is characterized by fast growth and extremely high recidivation rate (i.e., the percentage of patients with brain tumor recurrence following surgical macroscopic excision).

Malignant melanoma occurring in the CNS, primary or as metastasis, as well as malignant melanoma which primarily occurs in the skin and/or malignant melanoma which disseminates (metastasizes) further in the skin and/or in other body organs belong to nerve system derived tumors; cf. Shamamian et al., 1994, Cancer Immunol. Immunother. 39, 73-83; Florenes et al., 1994, Cancer Research, 54, 354-356. Malignant melanomas are derived from neuroectoderm, an embryonic layer. Burg et al., 1997, Deutsches Ärzteblatt 94, 890-895, describe a tumor growth inhibiting effect of tamoxifen for the malignant melanoma. Furthermore, glioblastoma and malignant melanoma have several tumor markers in common; cf. Shamamian et al., 1994, Cancer Immunol. Immunother. 39, 73-83; Florenes et al., 1994, Cancer Research 54, 354-356. In the case of metastases, the prognosis is very poor; cf. Burg et al., 1997, Deutsches Arzteblatt 94, 890-895.

Tumors originating in brain and/or nervous system and/or the meninges further comprise the neuroblastoma and the medullablastoma which in their entirety have been classified as the so-called primitive neuroectodermal tumors, abbreviated as PNET. These tumors further include the pinealoma originating in pineal body parenchyma and/or primordial germ cells in the pineal body region or the brain median.

Moreover, the pineal body is associated with the origin of craniopharyngeoma (a tumor producing β-HCG or LH-like glycoprotein, respectively; cf. Tachibana et al., 1994, J. of Neurosurgery 80, 79-84) which is considered to be an ectodermal tumor and originates in the front/upper face of the pituitary.

Both for craniopharyngeoma and meningeoma which is considered to be a benign tumor originating in arachnoidal cover cells and often adhering firmly to the inner surface of the meninges (dura mater), progesterone receptors and estrogen receptors have been described. Furthermore, androgen receptors have also been established in the case of meningeoma. In clinical studies using anti-progesterone medicaments, tumor-shrinking effects have been observed.

Up to now, the investigation of other therapies (different forms of chemotherapy, radiotherapy, etc.) in numerous clinical studies has failed to provide a substantial improvement of the prognosis for tumors originating in brain and/or nervous system and/or the meninges. At present, the standard therapy in the case of Glioblastoma multiforme consists of an as complete as possible surgical excision of the tumor followed by conventional radiotherapy. Under this standard therapy the statistically reported mean survival time is 9-13 months with individual variations and particularly a slightly better prognosis for younger patients having been observed.

About 30% of patients with recurrent Glioblastoma multiforme showed constant size or shrinking, respectively, of the inoperable residual brain tumor under sustained high-dosage of Tamoxifen, an anti-estrogen preparation. This tumor-inhibiting effect in glioblastoma treatment has not been attributed to its anti-estrogenic effect but to its inhibition of protein kinase C (an intracellular signal mediator); cf. Puchner et al., Zentralblatt für Neurochirurgie, Supplement 1996, 47. Jahrestagung Deutsche Gesellschaft für Neurochirurgie, page 44; Pollack et al., 1995, The Efficacy of Tamoxifen as an antiproliferative Agent in vitro for Benign and Malignant Pediatric Glial Tumors, Pediatr. Neurosurgery 22, 281-288). Moreover, Tamoxifen is said to increase the sensitivity of tumor cells for platinium-containing therapeutics as well as for radiotherapy.

For Glioblastoma multiforme (WHO grade IV astrocytoma) and for glioma with a lower grade of malignancy (WHO grade II-IV astrocytoma) steriod hormone receptors have been observed in a smaller percentage of the cases (cf. Paoletti et al., 1990, J. Neurosurgery, Characteristics and biological role of steroid hormone receptors in neuroepithelial tumors, 73, 736-742). Up to now, an indirect anti-proliferative effect in the case of Glioblastoma multiforme and glioma grade II-IV has been observed in clinical studies in only about 30% of the cases by a response of the tumor to Tamoxifen (an anti-estrogen preparation).

Although recently, several relatively reasonable new developments in Glioblastoma multiforme therapy have been described, the prognosis quod vitam for patients with Glioblastoma multiforme remains poor due to the extremely high recurrence rate despite the therapy forms tried and tested so far and due to the lack of a specific therapy and early diagnosis. The oat-cell carcinoma, another malignant tumor, is frequently found in lungs and is also derived from neural cells (Tecimer et al Arch. Pathol. Lab. Med., 124, 520-525, 2000).

BRIEF SUMMARY OF THE INVENTION

The invention relates to diagnostics which detect and/or determine GnRH receptors on tumor cells originating in brain and/or nervous system and/or the meninges and/or lungs and/or malignant melanoma and/or Kaposi sarcoma comprising contacting the cells with a ligand for a GnRH receptor and determining if binding has occurred.

Detection can be performed in an early stage of the tumor, thus reducing the time delay in surgical removal of the tumor and onset of the post-operative treatment.

In a preferred embodiment, the invention relates to a method for detecting GnRH receptors on malignant cells of a tumor originating in brain and/or nervous system and/or the meninges and/or of Kaposi sarcoma and/or oat-cell carcinoma. In a more preferred embodiment, the invention relates to a method for determining the relative number of GnRH receptors. The invention is further directed to providing a diagnostic kit for detecting GnRH receptor on tumor cells of tumors originating in brain and/or nervous system and/or the meninges and/or of Kaposi sarcoma, comprising a ligand for a GnRH receptor and a means for detecting bound ligand. The means for detecting bound ligands are known to a person skilled in the art and may comprise immunohistochemical staining methods and/or fluorescent or radioactive labels. The labels may be conjugated ligand and/or to antibodies directed against ligand and/or GnRH receptor.

The ligand of a GnRH receptor comprises a chemical compound, and/or an antibody, and/or a hormone, and/or a GnRH agonist and/or a GnRH antagonist and/or a functional part and/or derivative thereof, which binds to a GnRH receptor. A "functional part of a protein" is defined as a part which has the same kind of biological properties in kind, not necessarily in amount. By "biological properties" is meant the capability to bind to GnRH receptor. A "functional derivative of a protein" is defined as a protein which has been altered such that the biological properties of the molecule are essentially the same in kind, not necessarily in amount. A derivative can be provided in many ways, for instance through conservative amino acid substitution.

A person skilled in the art can generate analogous compounds of a protein. This can, for instance, be done through screening of a peptide library. Such an analogue has essentially the same biological properties of the protein in kind, not necessarily in amount. An "agonist of a GnRH receptor" comprises a chemical compound, and/or an antibody, and/or a hormone and/or a functional part and/or derivative thereof which combines with a GnRH receptor on a cell and initiates a physiological response in the cell as if the receptor had been activated by GnRH. An antagonist of a GnRH receptor comprises a chemical compound, and/or an antibody, and/or a hormone and/or a functional part and/or derivative thereof which combines with a GnRH receptor on a cell and at least partially, prevents physiological response in the cell.

The invention also includes a method of decreasing cellular replication of such tumors which results in a better prognosis for patients suffering from such a tumor. In a more preferred embodiment, the invention relates to a method for decreasing cellular replication of GnRH-positive glioma, oat-cell carcinoma, malignant melanoma, or Kaposi sarcoma comprising administering to a cell, a replication decreasing amount of a GnRH agonist. In a preferred embodiment, cellular replication is decreased in a patient suffering of the tumor. Therefore, the invention also provides for a method for decreasing cellular replication of GnRH-positive glioma, oat-cell carcinoma, malignant melanoma, or Kaposi sarcoma comprising administering to a subject a replication decreasing amount of a GnRH agonist. In a more preferred embodiment, replication is even more decreased by combining the replication decreasing ability of GnRH agonist with a cytotoxic substance. In a more preferred embodiment of the invention, the cytotoxic substance is coupled to the GnRH agonist.

The direct anti-proliferative effect of GnRH agonists on brain-derived tumors, e.g. Glioblastoma multiforme, has not been described to date. It has also been unknown that GnRH receptors are present on human ectodermal tumors, such as Glioblastoma multiforme. Furthermore, it has been unknown up to now that GnRH receptors are present on Kaposi sarcoma.

The present invention contributes to the improvement in diagnosis and therapy of tumors originating in brain and/or nervous system and/or the meninges and/or of Kaposi sarcoma and/or oat-cell carcinoma by providing a suitable target for diagnosis and therapy.

The invention is further directed to the use of diagnostic kits for the detection of GnRH receptors in immunohistological diagnostics and/or for the detection of GnRH receptor mRNA for monitoring of the therapy, aftercare for early recurrence detection during follow-up of the residual tumor still present after operation, for example a low grade glioma (G II-III WHO; cf. World Health Organization (WHO) classification of tumors of the central and peripheral nervous system, in: Kleihues et al., 1993, Histological Typing of Tumors of the Central Nervous System, Springer Verlag, Berlin-Heidelberg, New York-Tokyo) or for the detection of malignization in the sense of a Glioblastoma multiforme (G IV), and for early detection in risk groups for screening for the presence of tumors, such as Glioblastoma multiforme, originating in brain and/or nervous system and/or the meninges.

The kit according to the present invention may be used to detect GnRH receptors on cell membranes or in body liquids, such as blood, plasma, serum, urine or liquor, tissue extracts, tissue liquids, in vitro cell culture supernatants and cell lysates. The GnRH receptor may for example be determined immunohistochemically on, for example, operatively excised tumor preparations or tissue cultures or, by means of a conventional radioimmuno assay, for example in body liquids. The diagnostic kit comprises a GnRH agonist and/or a GnRH antagonist and/or a monoclonal or polyclonal antibody against human GnRH receptors and/or one or more specific primers against GnRH receptors for example for the amplification of the cDNA of a GnRH receptor in a reverse transcriptase-polymerase chain reaction (RT-PCR). Detection of GnRH receptors is conducted in a manner known per se using well known immunological assays, in particular using enzyme-linked immunoadsorbent assays (ELISA), or in a particular embodiment using the methods described below for the detection and determination of GnRH receptors on degenerate cells.

BRIEF DESCRIPTION OF THE DRAWINGS

FIG. 12: A) RT-PCR evaluation of the expression of GnRH receptor mRNA in U87 glioblastoma cells (lane 1), prostate cancer cells (lane 2). And human pituitary (lane 3). Lane 4, RT-PCR amplification control. B) Western blot analysis of GnRH receptor protein in U87 glioblastoma cells (lane 1) and prostate cancer cells (lane 2). C) Effects of GnRH agonist (ZOLADEX®) on U87 glioblastoma cell proliferation. Data are mean ±SE * p, 0.05 vs. C, controls. The results obtained in one out of three experiments are reported in A and B.

DETAILED DESCRIPTION OF THE INVENTION

Figure 1:
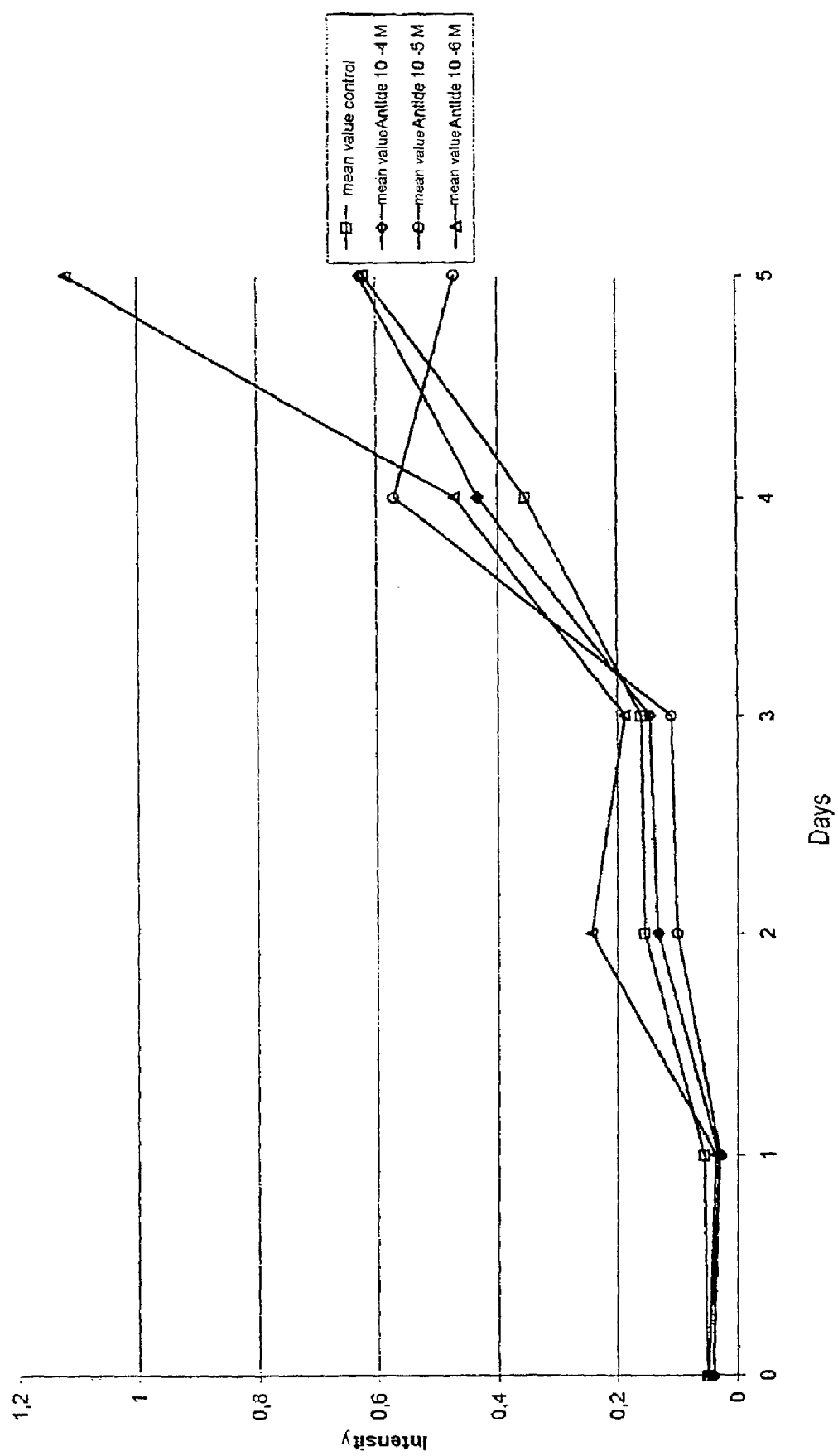
FIG. 1: Inhibition of proliferation on malignant melanoma MV3 cells by Antide (GnRH antagonist).

In a preferred embodiment, the present invention relates to a method for the detection and/or determination of GnRH receptors on degenerate cells of a tumor originating in brain and/or nervous system and/or the meninges comprises the following steps of: a) homogenizing peroperatively obtained tumor tissue, b) separating the membrane fraction, c) determination of the protein concentration in the membrane fraction of b), d) determination of the concentration of GnRH receptors in the membrane fraction of b). The present method is particularly useful for the detection and/or determination of GnRH receptors in tissue derived from Glioblastoma multiforme, medulloblastoma, pinealoma, neuroblastoma, craniopharyngeoma, meningeoma, chordoma, Ewing sarcoma, malignant melanoma, oat-cell carcinoma, or Kaposi sarcoma. This method provides a method to diagnose tumors.

In a particularly preferred embodiment, fresh human tumor tissue is collected for example during brain tumor surgery ("preoperatively") followed by storage in liquid nitrogen. For GnRH receptor determination, the frozen tissue samples are ground and homogenized. In a centrifugation step, the samples are separated from larger tissue debris. The supernatant is again centrifuged. The resulting sediment (pellet) contains the membrane fraction which is again homogenized to obtain an as homogenous membrane suspension as possible. The membrane suspension is used in the radio receptor assay for determination of GnRH receptors. First, the protein concentration in the membrane fraction prepared is determined photometrically in a conventional and known manner e.g. using the BioRad protein assay (BioRad, Munich). Determination of the GnRH receptor concentration is performed using a known GnRH agonist, such as Buserelin binding specifically to GnRH receptors in the membrane fraction prepared. Since the GnRH agonist has been radiolabeled, for example by $^{125}$I, the concentration of bound radiolabeled GnRH agonist mirrors the concentration of GnRH receptors in the membrane fraction. The concentration of bound radiolabeled GnRH agonist is determined by means of radioactive counts per minute. Both low affinity/high capacity and high affinity/low capacity GnRH receptor binding sites are evaluated (cf. Baumann, K., et al., 1993, Breast Cancer Research Treatment, vol. 25, page 37-46).

GnRH receptors as well as a GnRH agonist treatment have so far been described neither for craniopharyngeoma nor for meningeoma or oat-cell carcinoma, or chordoma or Ewing sarcoma or malignant melanoma and also not for the Kaposi sarcoma. For these tumors, no blood-brain barrier exists, since they originally are extracerebral, intracranial or peripheral tumors. Therefore, the therapy according to the present invention using GnRH agonists or conjugates thereof, is very advantageous. However, the blood-brain-barrier is permeable for GnRH since a two-direction-system, a bi-directional active transport of GnRH across the blood-brain-barrier exists (Barrera, C., Banks, W. A., Fasold, M. B., and Kastin, A. J., 1991, Effects of Various Reproductive Hormones on the Penetration of LHRH Across the Blood-Brain Barrier, Pharmacology, Biochemistry & Behaviour, vol. 41, 255-257). Thus the treatment by GnRH agonists has advantages over the treatment with Tamoxifen for which a blood-brain-barrier exists. For Ewing sarcoma and other peripheral forms of PNET outside of the nervous system, for malignant melanoma and for Kaposi sarcoma, the blood-brain-barrier generally does not play an essential role in the treatment with GnRH agonists since these tumors in most of the cases arise and stay on the outside of the blood-brain-barrier.

The invention further relates to a method for decreasing cellular replication of GnRH-positive glioma, oat-cell carcinoma, malignant melanoma, or Kaposi sarcoma comprising administering to a cell a replication decreasing amount of a GnRH agonist. In particular, the invention relates to a method for decreasing cellular replication of GnRH-positive glioma, oat-cell carcinoma, malignant melanoma, or Kaposi sarcoma comprising administering to a subject a replication decreasing amount of a GnRH agonist. In a preferred embodiment, the method for decreasing cellular replication of GnRH-positive glioma, oat-cell carcinoma, malignant melanoma, or Kaposi sarcoma also comprises administering a cytotoxic substance, such as a radioisotope, or another toxic substance such as ricin A or the like. The cytotoxic substance is preferably coupled or conjugated to the GnRH agonist.

TABLE I

List of GnRH agonists which may be employed in the treatment of a tumor having GnRH receptors and originating in brain and/or nervous system and/or the meninges and/or of Kaposi sarcoma:

GnRH agonists:
Pharmacological substance name

Leuprorelinacetate, Leuprorelin
Triptorelinacetate, Triptorelin
Buserelinacetate, Buserelin
Goserelinacetate, Goserelin The minimum treatment dose of the GnRH agonists in Table 1 corresponds to the dosage cited in the ROTE LISTE® for the respective GnRH agonists for other indications of use for the subcutaneous or the intramuscular administration form, respectively. For intravenous administration of GnRH agonists the minimal daily dose is employed, cf. for example Klijn et al., 1982, The Lancet, 1213-1216.

According to the invention, GnRH agonists may be employed in any suitable form. For tumors within the blood-brain-barrier, direct injection, e.g. into the circulation, intra-arterially directly into the nervous system circulation or intravenously, or injection in the liquor ways or local application in the tumor bed following surgery, directly after macroscopic tumor resection, peroperatively or with OMMAYA® reservoir, or another form of subcutaneous ventricular injection in the liquor ways is preferred. It is possible to use both GnRH agonists because both bind as ligands to the GnRH receptor. Further, ligands which are specifically directed to the GnRH receptor may be used, for example, preferably human or humanized antibodies. In most cases it is preferable to ensure that the targeting agent primarily reaches tumor cells. Therefore, imaging methods using the ligand with tracers are a further aspect of the invention. If the ligand is localized mainly in the tumor, the ligand may be coupled to a cytotoxic agent, such as a radioisotope or another toxic substance such as ricin A or the like. Preferred GnRH agonists are cited in the ROTE LISTE® which is explicitly incorporated herein by reference (ROTE LISTE®, 1997, paragraph 50, part 3, pituitary hormones, 50038 to 50056, editor ROTE LISTE® Service GmbH, Frankfurt/Main).

The above-mentioned GnRH agonists may be administered in dosages approved for other treatments. There may also be used dosages established during dose finding studies for the use of similar materials (substances, medicaments) such as somatostatin analogues in pituitary adenoma, glioblastoma or pancreas adenocarcinoma, or for phase II studies with GnRH analogues (agonists or antagonists) for other indications, for example, mammary carcinoma, prostate carcinoma or ovarian carcinoma.

In a particular embodiment, the GnRH agonists are conjugated with a gonadotropin or LH inhibitor, respectively, such as Gossypol (cf. Flack et al., 1993, J. Endocrinol. Metab., Oral Gossypol in the Treatment of Metastatic Adrenal Cancer 76, 1019-1024; Poso, H., et al., The Lancet, 1980, 885) or with melatonin or a melatonin analogue (an agonist or antagonist) (cf. Lissoni et al., 1996, Increased Survival Time in Brain Glioblastomas by a Radioneuroendocrine Strategy with Radiotherapy plus Melatonin Compared to Radiotherapy Alone, Oncology 53, 43-46).

In the following an example for a preferred treatment protocol is described.

For the first time, the GnRH receptor concentration in cell membranes of human brain or nervous system tumor cells, i.e. the GnRH receptors on the membrane which are effective in vitro have been determined using a radio receptor assay. With the method according to the invention, the biological activity or specifically the active GnRH receptors, respectively, are determined. For this purpose, radiolabeled Buserelin, a GnRH agonist, is used as a marker binding specifically to GnRH receptors. Based on radioactive counts of bound Buserelin the GnRH receptor concentration may be determined. This detection has already been used for other tumors such as mammary carcinoma and the like. The method used according to the present invention measures the GnRH receptor concentration on cell membrane extracts of fresh human tumor tissue.

During preoperative resection of the tumor, tissue is obtained and processed for pathological anatomical examination and for GnRH receptor determination, e.g. in the manner described herein. Following pathological anatomical examination and confirmation of the histological diagnosis of a tumor originating in brain and/or nervous system and/or the meninges and/or of Kaposi sarcoma a prognosis may be made for a therapy success during treatment with GnRH agonists with respect to the concentration of GnRH receptors present.

At a concentration of the GnRH receptor of more than 1000 amol/mg (=1 fmol/mg) membrane protein the patient will be diagnosed as GnRH receptor-positive. Being not GnRH receptor-positive is no criterion for exclusion from treatment since no clinical exclusion criteria exist for GnRH agonist treatment. The being GnRH receptor-positive of a patient is judged prognostically as a faster tendency of recidivation than that of being GnRH receptor-negative in the course of tumor growth under classical standard treatment wherein the GnRH receptor functions as a prognostic tumor marker. Also, being GnRH receptor-positive is considered to be particularly advantageous for the treatment with GnRH agonists, and being GnRH receptor-positive or -negative provides a prognostic information of the therapy success to be expected so that GnRH receptor is a prognostic tumor marker in that treatment. The GnRH agonist treatment is started immediately after pathological anatomical examination, e.g. postoperatively in the case of rapid section pathological diagnostics.

Following determination of the presence of GnRH receptors, a suitable ligand (GnRH agonist, or conjugates) is selected and administered to the patient from whom the tumor was derived, preferably after diagnostic imaging methods. Cf. MTT test literature: Hunter et al., 1993, Europ. J. Surg. Oncology, 242-249.

The treatment is continued as long as no complete remission has occurred. Criteria to judge the therapy effect are: (A) tumor volume on MRT images and/or CAT scan images, (B) recidivation-free survival, (C) overall survival for initial application as well as (D) Kamofsky and Spitzer indices. The dosage for administration which may be in any suitable form known to those skilled in the art is described above and below in this patent application.

The exact mechanism of action of GnRH agonists on tumors is unknown. For the tumor types known so far having active GnRH receptors such as mammary carcinoma, prostate carcinoma and ovarian carcinoma, a locally regulatory autocrine-paracrine system has been proposed in the literature; cf. Irmer et al., 1995, Cancer Research 55, 817-822. For the tumors mentioned, anti-proliferative activities of GnRH agonists or GnRH antagonists have been described in the literature, both in vitro (Palyi et al., 1996, Cancer Detection and Prevention, 20, 146-152; Irmer et al., 1995, Cancer Research, 55, 817-822; Pati et al., 1995, Endocrinology, 136, 75-84) and in vivo or clinically, respectively; cf. Gonzalez-Barcena et al., 1994, The prostate 24, 84-92; Jonat et al., 1995, European J. of Cancer, 31A, 137-142; Emons and Schally, 1994, Human Reproduction Update 9, No. 7, 1364-1379; wherein this anti-proliferative activity goes beyond the anti-proliferative effect to be expected of reversible "chemical castration" by GnRH agonists.

For glioblastoma and glioma in a similar manner the following mechanism of action can be considered. In the literature (Constam et al., 1992, J. Immunology, 148, 1404-1410) the production of transforming growth factor $\beta$ (TGF-$\beta$) by glioblastoma cells has been described. Growth factor TGF-$\beta$ has been described by Melcangi et al., 1995, Endocrinology, 136, 679-686, as a product of rat glia cells, i.e., normal non-tumor cells, which as a factor in vitro stimulates the natural GnRH production in hypothalamic cells. It has been postulated that GnRH produced and secreted locally by glioblastoma has a stimulating effect on the tumor growth which has also been known for TGF-$\beta$. Also human glioblastoma cells and glioma cells, respectively, are able to secrete circulating immunosuppressive substances, mainly TGF-$\beta$, and therefore may induce an adverse effect on cellular immune reactions. Besides a GnRH-stimulating function, the increase in TGF-$\beta$ presumably also has an immunosuppressive (defense inhibiting) effect on the cellular immunity of the patient due to which tumor growth is promoted and tumor size increases. For Glioblastoma multiforme, medulloblastoma, and malignant melanoma, this immunosuppressive phenomenon of TGF-$\beta$ has been described; cf. Stockhammer et al., 1995, J. of Neurosurgery 83, 672-681; Jennings et al., 1994, Hum. Pathol. 25, 464-475; Bizik et al., 1996, J. Cell Biochem. 62, 113-122; van Belle et al., 1996, Am. J. Pathol. 148, 1887-1894. This autocrine-paracrine growth regulating system may be reversed resulting in a decrease in tumor size. This reversion (also referred to as "negative feedback" in endocrinology) may be in principle effected by an excess of GnRH (competitive inhibition). This effect is even enhanced by using GnRH agonists or GnRH antagonists instead of GnRH. A result of this therapy is a decrease in TGF-$\beta$ production followed by a decrease in tumor size resulting therefrom. Also $\beta$-HCG plays an immunosuppressive role. According to the invention, also the LH-$\beta$ and $\beta$-HCG production, respectively, are inhibited by GnRH agonists or GnRH antagonists. Also, in GBM the EGF production is inhibited.

For the tumors originating in brain and/or nervous system and/or the meninges belonging to indication invention, reference is made to the World Health Organization (WHO) classification of tumors of the central nervous system which has been established in 1990 (Kleihues et al., 1993, Histological Typing of Tumors of the central nervous system, Springer Verlag, Berlin Heidelberg New York Tokyo). In addition to the tumors cited in the above-mentioned WHO classification, also malignant melanoma, Ewing sarcoma and the Kaposi sarcoma belong to the indication invention. Excluded from the indication invention are the pituitary adenoma, all metastases except Ewing sarcoma, melanoma and Kaposi sarcoma, lymphomas and hematopoietic tumors. Germ cell tumors such as chorion carcinoma are similar to malignant tumors of the placenta which are known for bearing GnRH receptors. Therefore, the germ cell tumors of the central nervous system belong to the present indication invention. The Kaposi sarcoma with multicentric occurrence in the body consists of cells of monoclonal origin (Rabkin et al., 1996, The New England Journal of medicine, 14, 988-993). It has specific antigens in common with skin neurofibroma, a tumor originating in the nervous system (Rudolph, P., et al., 1997, Am. J. Surg. Pathol. (US), 21(7), 791-800).

With respect to hormones, Kaposi sarcoma is similar to malignant placental tumors and meningeoma since Kaposi sarcoma has β-HCG receptors as have these tumors and reacts anti-proliferatively to the administration of β-HCG as for example does the meningeoma (Boyle-Wash et al., 1995, Effect of glycoprotein and protein hormones on human meningeoma cell proliferation in vitro, Journal of Endocrinology, 145, 155-161; Albini et al., 1997, The beta-core Fragment of human chorionic gonadotropin inhibits growth of Kaposi sarcoma-derived cells and a new immortalized Kaposi sarcoma cell line, AIDS (US), 11(6), 713-721; Gill et al., 1996, The effects of preparations of human chorionic gonadotropin on aids-related Kaposi sarcoma, The New England Journal of Medicine, 335 (17), 1261-1269). Due to the analogy to meningeoma, Kaposi sarcoma has GnRH receptors wherein the discovered autocrine connection of GnRH being known as the β-HCG releasing hormone in placenta and placental tumors plays a role (Lin et al., 1995, J. Clin. Endocrinol. Metab. 80, 580-585). The tumors cited above in the WHO classification of central nervous system tumors as well as malignant melanoma with β-HCG production and/or β-HCG receptors carry GnRH receptors. The Ewing sarcoma belongs to the group of primitive neuroectodermal tumors (PNET) and is a peripheral form of these (Grier, H. E., 1997, The Ewing Family of Tumors. Ewing sarcoma and primitive neuroectodermal tumors. Pediatric Clin. North Am. (US), 44 (4), 991-4).

The pineal gland (Glandula pinealis) is the origin of the production of the hormone melatonin which is a GnRH receptor expression stimulating hormone in metastasizing prostate carcinoma in the case of resistance during a GnRH agonist treatment (cf. Lissoni et al., 1997, European Urology 31, 178-181) and in addition has an anti-angiogenetic activity (Regelson, W., Pierpaoli, W., 1987, Cancer Invest., 5, 379-385). GnRH agonists and GnRH antagonists have an anti-mitotic and anti-proliferative activity, respectively, by inhibiting growth factors such as epidermal growth factor (Motta et al., 1996, J. Steroid Biochem. Molec. Biol., 56, 107-11, 1996). Epidermal growth factor is also present as a mitogen and, thus, as a positive growth factor, e.g., in Glioblastoma multiforme (Rao et al., 1996, Peptides (US), 17, 179-181). Thus, a melatonin-GnRH analogue conjugate reasonably combines an anti-mitotic and anti-angiogenetic activity on tumors such as glioblastoma and induces the further expression of GnRH receptors e.g. in Glioblastoma multiforme in order to avoid resistance against GnRH agonist/GnRH antagonist treatment by GnRH receptor depletion.

According to the present invention there are provided for the first time GnRH agonists for the preparation of a medicament for the treatment of tumors originating in brain and/or nervous system and/or the meninges and/or of Kaposi sarcoma.

According to the invention, the GnRH agonists as well as the conjugated GnRH agonists are used to treat tumors originating in brain and/or nervous system and/or the meninges, for example Glioblastoma multiforme. The medicaments according to the present invention may be prepared in any manner known to the skilled artisan, in particular for subcutaneous, intramuscular, intravenous, intraspinal or subdural, respectively, or intranasal application or in the form of a sustained release implantation. The medicaments according to the present invention may also be administered via a subcutaneous ventricular cytostatic reservoir being connected to the ventricle wherein the reservoir may be replenished by injections through the skin. The GnRH agonists may be administered in the same dosage as those which are for example used in the treatment of prostate, mammary carcinoma or endometriosis; cf. e.g. ROTE LISTE®, 1997, paragraph 50, part 3, hypothalamic hormones, 50038 to 50056, Editor ROTE LISTE® Service GmbH, Frankfurt/Main, which is included herein explicitly by reference; cf. Annex A. The minimal dose corresponds to the dose cited in the Rote Liste for the respective GnRH agonists. For example, in the case of intraspinal or subcutaneous ventricular administration via a cytostatic reservoir the minimal dosage may be lower than that cited in the ROTE LISTE® for the respective GnRH agonists. The maximal dose corresponds to the $LD_{50}$ value for the respective GnRH agonists. The dosage may be optionally increased or decreased following a finding of the GnRH receptor concentration obtained in a neurological manner. The frequency of application or daily dose, respectively, may also be found in the ROTE LISTE®. Preferably, the medicaments are administered until complete remission (regression) of the tumor which may be evaluated neuroradiologically and clinically.

For subcutaneous administration, e.g. CARCINIL®, DECAPEPTYL® 0.5 mg/0.1 mg or Uno-Enantone may be employed. As sustained release implantations for example PROFACT®-DEPOT, ZOLADEX®, or ENANTONE MONATS-DEPOT® may be administered. For intramuscular administration, e.g. DECAPEPTYL®-DEPOT, DECAPEPTYL®-GYN, or Enantone-Gyn may be employed. For intranasal administration e.g. PROFACT®-NASAL, SUPRECUR®-NASAL, or SYNARELA®-NASAL may be used. For intravenous administration or intranasal administration, respectively, for example PROFACT® pro injectione/-nasal may be administered in the dosage given by Klijn, J. G., and De Jong, F. H. in Klijn, J. G., and De Jong, F. H., 1982, The Lancet, 1213-1216.

The following examples are intended to illustrate the invention and should not be construed as limiting the invention.

EXAMPLES

Example 1

Determination of the Concentration of GnRH Receptors

As an example for the determination of the concentration of GnRH receptors on cell membrane extracts of cell lines and/or cell cultures, the Decapeptyl® radio receptor assay is used with membranes (as described by Emons, G., et al., 1993, Cancer Research 53, 5439-5446). According to this protocol, the GnRH receptors are determined on a human cell line such as the human glioblastoma cell line U-87 MG or U-373MG (Pinski et al., 1994, Cancer Research 54, 5895-5901). In this test, the low affinity/high capacity as well as the high affinity/low capacity GnRH receptor binding sites are evaluated. Similar results as those described in Emons, G., et al., supra, for the cell lines EFO-21 and EFO-27 are obtained.

As another example for the determination of the concentration of GnRH receptors on cell membrane extracts of cell lines and/or cell cultures the LHRH radio receptor assay with labeled Triptorelin (Emons, G., et al., supra) is performed on a Kaposi sarcoma cell line such as the well known cell line KSY-1 or KS-SLK (Parkash et al., 1996, New England Journal of Medicine 335, 17, 1261-1269) and on a human malignant melanoma cell line such as the well known cell lines MV3 and BLM (Goldbrunner, R. H., et al., 1996, Anticancer Research 16 (6B), 3679-3687) obtaining similar results for the GnRH receptor determinations as described in Emons, G., et al., supra, for the cell lines EFO-21 and EFO-27.

Characterization of ligands of the GnRH receptor (GnRHR) isoforms on glioblastoma cells.

Cultured glioblastoma cells are washed with buffer and completely lysed under conditions that suspend all membrane proteins. This requires the addition of mild detergents (e.g. NP40). Next the suspension is mixed with a lysate of cells or tissue, in which the ligand is to be detected. The cells may originate from hypothalamic tissue or from a tumor or from cultured cells thereof. Next an antibody, which is specifically directed against the GnRHR is added in order to form a complex with GnRHR and the ligand. The monoclonal anti-GnRHR antibody published by Karande et al., is used for this purpose. Next the complex between the antibody, the GnRHR and the ligand is purified from the solution. This is done by adding solid beads coupled to Protein G (e.g. Protein G sepharose from Pharmacia) and short centrifugation. Next the proteins of the bead-coupled complex of Protein G, GnRHR and ligand is preparatively separated. This is performed by electrophoresis or chromatography. The bands of the electrophoretic gel or the eluted peaks of the chromatography are characterized. For this, standard methods like protein sequencing and/or mass spectroscopy are suitable. The resulting sequence or the determined exact mass is compared with the data of known proteins using standard databases. This leads to the identification of the yet unknown ligand of the GnRHR.

Example 2

Determination of the mRNA of GnRH Receptors by Means of RT-PCR

As an example for the determination of GnRH receptor messenger RNA by means of RT-PCR for example RNA from the glioblastoma cell line U-87 MG or U-373MG is in a first reaction transcribed to cDNA. In a further reaction, for example, the 884 bp fragment of the pituitary GnRH receptor (Kakar, S., et al., Biochem. Biophys. Res. Comm., 1992, 289-295) or of the placental GnRH receptor (Leung, P. C. K., Biological Signals, 1996, 5, 63-69) or of the placental GnRH receptor gene (Lin, L., et al., J. Clinical Endocrinol. Metabolism, 1995, vol. 80, No. 2, 581-584) is amplified using specific primers in a reverse transcriptase polymerase chain reaction wherein the cDNA of a known GnRH receptor-positive cell line serves as the positive control. Then, the reaction products are visualized in a polyacrylamide (PAA) gel. On the PAA gel in lane 1 there may be seen the fragment length marker, in lane 2 a clear band of the 884 bp GnRH receptor PCR product in the MCF 7 positive control and also in the lane of the glioblastoma cell line a signal of an 884 bp product or other GnRH receptor splice variant (fragment) signals. This mRNA detection is performed similar to other GnRH receptor mRNA determinations, see for example Irmer et al., 1995, Cancer Research, 55, 817-822.

Example 3

Therapeutic in vitro Study

Proliferation Assay on Cell Cultures

A human cell line such as the well known human glioblastoma cell lines U-87MG or U-373MG (Pinski et al., supra) or a human cell line such as the well known Kaposi sarcoma cell lines KSY-1 or KS-SLK (Parkash et al., 1996, New England Journal of Medicine, 335, 17, 1261-1269) or a human cell line such as the well known human malignant melanoma cell line MV3 or BLM (Goldbrunner, R. H., et al., 1996, Anticancer Research 16 (6B), 3679-87) or a human medulloblastoma cell line such as the well known cell line Daoy or D283 MED (Stockhammer et al., 1995, J. Neurosurgery, 83, 672-681) or human meningeoma cell cultures (Boyle-Wash, E., et al., 1995, Journal of Endocrinology, 145, 155-161) are cultured as described by the above-mentioned authors for the above-mentioned cell lines and then treated as described by Emons, G., et al., 1993, supra, and Irmer, G., 1995, supra, with a concentration of the GnRH agonist Triptorelin, GnHR antagonist SB-75 (Cetrorelix) or GnRH antagonist Ramorelix as described therein. Similar results to those described by Emons et al., Cancer Research, 53, 1993, 539-544, and Irmer, G., et al., supra, were obtained.

Separately, the above-mentioned cell lines were also treated with an GnRH agonist, either with GOSERELIN® (ZOLADEX®, Buserelin or LEUPRORELIN®) or with a GnRH antagonist such as Antide® or Antarelix®. Similar anti-proliferative effects as those described by Pinski et al., or Irmer et al., supra, were observed.

Also separately, such cell lines were additionally treated each with one of the GnRH antagonists Cetrorelix®, Antarelix®, Antide®, and Ramorelix® or with one of the GnRH antagonists as described in U.S. Pat. No. 5,480,969, U.S. Pat. No. 5,198,533, or UK Patent GB 2 246782 B wherein this treatment was performed similar to that reported in Emons et al., supra, for SB 75 (Cetrorelix). A similar anti-proliferative effect occurs.

The cell lines cited above were also treated separately with monoclonal antibodies against a GnRH receptor antigen as described by Karande, A. A., et al., 1995, Mol. Cell. Endocrinol. 114 (1-2), p. 51-56. A similar anti-proliferative effect is observed for the above cell lines as has been described by Ackermann, R. C., et al., 1994, Cancer Letters, 81, 177-184, for the OVCAR-3 cell line.

Example 4

In vivo Study in the Model of Xenotransplantation

An in vivo Study with Nude Mice

An effect of the treatment of tumor-implanted nude mice (Pinski et al., supra) each with one of the GnRH agonists Buserelin, Triptorelin, Goserelin, and Leuprorelin and each with one of the GnRH antagonists Cetrorelix (SB-75), Antarelix®, Antide®, and Ramorelix® on the growth of malignant gliomas U-87 MG and U-373MG was proven by us using daily doses and controls in nude mice as have been described for the determination of the efficacy of similar peptides in Pinski et al., supra. Similar growth-inhibiting effects could be observed in the above tumors by treatment with the GnRH agonists and GnRH antagonists mentioned by us.

Example 5

Phase I Study

Patients with non-resectable Glioblastoma multiforme in the condition after microsurgical resection and/or after external conventional radiotherapy and/or brachytherapy or patients with a diffusely, intraaxially growing brain tumor, multifocal tumor spreading or presence of a gliomatosis cerebri, respectively, a tumor volume of more than 65 ml or a minimal tumor diameter of more than 5 cm were treated with the GnRH agonist Buserelin administered intravenously as described by Klijn, J. G. M., et al., 1982, The Lancet, May 19, 12143-1214, and also as described therein by intranasal application as a permanent medication. As the effect of the treatment a reduction in tumor volume is observed on MRT or CT images, respectively. A recidivation-free survival longer than described for the tamoxifen treatment method of glioma (Pollack et al., 1995, Pediatr. Neurosurgery 22, 281-288) has been observed.

Example 6

Phase I Study

Patients with inoperable, stereotactically confirmed Glioblastoma multiforme after conventional radiotherapy were treated under permanent medication with ZOLADEX® in the dosage and administration form as cited for metastasizing mammary carcinoma in the ROTE LISTE®. MRT controls reveal a significant reduction in tumor volume.

Example 7

Phase II Study

Patients with histologically confirmed Glioblastoma multiforme after a first operation were treated (randomized controlled) with ZOLADEX® as described by Jonat et al., 1995, European J. Cancer, 137-142. Following radiotherapy, they are assigned to two groups. One group is treated with ZOLADEX® and one group without ZOLADEX® (or with Cetrorelix and without Cetrorelix, or with ANTIDE® and without ANTIDE®, or with DECAPEPTYL® or without DECAPEPTYL® etc.). The effects are similar to the metastasized perimenopausal mammary carcinoma. The percentage showing an actual significant therapy effect is evaluated according to the criteria of tumor volume, recidivation-free survival, overall survival following initial application and Karnofsky and Spitzer indices in a clinical neurological examination and under consideration of the other examination criteria (Sposto, R., et al., 1989, J. Neurooncology, 7, 165-177, and Kirby, S., et al., 1995, J. Natl. Cancer Institute, 87, 1884-1888, 1995). In MRT and/or CAT scan, a significantly higher reduction in tumor volume or significantly longer recidivation-free survival and significantly longer overall survival following initial application, respectively, than in the control group not treated with ZOLADEX® have been observed.

By using a method of gene therapy well-known to the skilled artisan retroviruses and antisense GnRH receptor vectors are stably transfected into glioma cells, and an antiproliferative effect is observed.

Example 8

Collection of Glioma Tissue

During brain tumor operations (peroperatively) fresh human tumor tissue was collected dry in a small sterile dish without addition of medium and immediately transferred into a sterile standard plastic tube. The tube was sealed air-tight and after about 15 minutes shock-frozen in a Dewar container (Union Carbide Cryogenic Equipment 35HC, ref. No. 103-139-T5) containing liquid nitrogen. The tissue samples were stored in liquid nitrogen for about 2 months until GnRH receptor determination.

Example 9

Tissue Preparation

The frozen tissue samples were cleaned from residual blood and fat and cut into pieces of about 2×2×2 mm using a scalpel. The tissue samples were homogenized for 1 minute at maximum output in a Dismembrator II (B. Braun, Melsungen). The homogenized tissue was resuspended in 1000 µl of cold buffer 1 (10 mM tris-(hydroxymethyl)-aminomethane, pH 7.4, 4° C.) and mixed as homogenous as possible. In a first centrifugation step (800×g, 10 minutes, 4° C.) the sample was separated from larger tissue debris. The supernatant was again centrifuged (10.000×g, 45 minutes, 4° C.). The supernatant of the second centrifugation step was discarded, and the pellet containing the membrane fraction was resuspended in 1000 µl of cold buffer 1 and homogenized using a Polytron homogenizer three times for 4 seconds each to obtain an as homogenous membrane suspension as possible. To this membrane fraction, 1000 µl of cold buffer 1 were added. This suspension was used in the determination of GnRH receptors in the radio receptor assay.

Example 10

Determination of the Protein Concentration

The BioRad reagent was diluted 1:5 with distilled water 3.5 ml of this reagent were mixed with 50 µl of the membrane fraction prepared and incubated for 5 minutes. Photometric measurement of the protein concentration was carried out as a double determination at a lambda of 595 nm in a well-known manner. A human albumin protein standard which is correspondingly used for the measurement serves as the protein standard.

Example 11

The Radio Receptor Assay

The determination of the concentration of GnRH receptors was carried out in the membrane fraction of the tissue prepared as described above. The radio receptor assay comprised two different samples each of which is determined in four-fold: a) samples containing the prepared membrane fraction, and b) control samples.

a) 300 µl buffer 2 (10 mM tris-(hydroxymethyl)-aminomethane, pH 7.4, 0.1% bovine serum albumin) and 100 µl of tracer ($^{125}$I-Buserelin, 80.000 cpm/100 µl) were added to 100 µl of membrane fraction.

b) For the controls, 250 µl buffer 2, 100 µl of tracer, 100 µl of membrane fraction and 50 µl GnRH analogue ($10^{-5}$ M Buserelin) are mixed.

The individual samples were well mixed and then incubated for 90 minutes at 4° C. The radio receptor assay was stopped by addition of 500 µl of bovine gamma globulin solution (0.1% bovine gamma globulin, 0.15 M NaCl). Subsequently, 1000 µl of a 25% PEG-6000, 0.15 M NaCl solution were added.

The samples were again mixed until homogenous and incubated for 20 min at 4° C. Separation of the PEG-hormone receptor complexes was performed via a centrifugation step (1.600×g, 30 minutes, 4° C.) during which the complexes due to their higher mass form the pellet. The supernatant is removed carefully using a Pasteur pipette. The number of counts per minute serving as a basis for evaluation of the GnRH receptor content was then determined in a Gamma counter (Berthold).

Example 12

Examination of the Radio Receptor Assay

Generally, several tissue samples were used in an experimental approach. To exclude a systematic error in the case of a negative result of all samples in one assay, a standard sample from bovine pituitary tissue was examined in each of the assays in parallel to the tumor tissues. Thus, the detection of GnRH receptors in bovine pituitary tissues served as a positive control. The pituitary tissue was prepared similar to the tumor tissues and the membrane fraction was purified in a similar manner.

Example 13

Evaluation of the GnRH Receptor Content

The evaluation of the GnRH receptor content (fmol/mg of membrane protein) was carried out on the basis of the counts per minute (cpm), the specific binding, the amount of protein used, and the specific activity of the radiolabeled ligand.

The specific binding ($B_{spec}$) is calculated from the difference of the mean value of the fourfold determination of total binding ($B_0$) and the mean value of the fourfold determination of unspecific binding (NSB).

The amount of protein used is determined photometrically as described above under 3.

Data of the analogue $^{125}$I-Buserelin:

| MG: | 1253 g/mole |
|---|---|
| Specific Activity: | 1470 mCi/mg |
| Activity of $^{125}$I-Buserelin solution | 20 µCi/ml |

1470 mCi/mg $^{125}$I-Buserelin = 54.4 × 10$^9$ Bq/mg
1 ml of $^{125}$I-Buserelin solution includes 13.61 × 10$^{-9}$ g $^{125}$I-Buserelin with 7.4 × 10$^6$ Bq
13.61 × 10$^{-9}$ g/ml $^{125}$I-Buserelin = 10.9 × 10$^{-12}$ mole $^{125}$I-Buserelin, 54.4 × 10$^9$ Bq = 44.4 × 10$^7$ cpm.
10.90 × 10$^{-12}$ mole $^{125}$I-Buserelin = 44.4 × 10$^7$ cpm
1000 cpm correspond to 0.247 × 10$^{-15}$ mole $^{125}$I-Buserelin.

For the calculation of the GnRH receptor concentration (fmol/mg of membrane protein) from the cpm values measured also the amount of protein used and the disintegration factor has to be considered. Thus, the equation for the calculation of the GnRH receptor content is the following:

$$\frac{0.247 \times 10^{-15} \text{ mole }^{125}\text{I-Buserelin}}{\text{disintegration factor} \times \text{amount of protein}} = 1000 \text{ cpm}$$

TABLE II

Determination of the GnRH concentration
The results of the GnRH receptor determination using the radio receptor assay according to the invention of tissue samples of several patients are listed.

| | ER fmol/ mg prot | PgR Fmol/ mg prot | GnRH rec. atomol/ mg prot | Finding |
|---|---|---|---|---|
| Histological samples | 10 | 20 | 1000 | negative |
| | 10-20 | 20-30 | 1000-3000 | weakly positive |
| | 20 | 30 | 3000-5000 | positive |
| | 50 | 100 | 5000 | strongly positive |
| Chordoma | 1 | 1 | 708 | |
| GBM | 1 | 2 | 2478 | |
| GBM | 1 | 1 | 895 | |
| GBM | 1 | 1 | 1111 | |
| G II Glioma | 1 | 1 | 3635 | |
| Meningeoma | 1 | 74 | 1 | |
| Adenocarcinoma | 1 | 1 | 1 | |
| GBM Fibrillary | 1 | 1 | 7357 | |
| G II Astrocytoma | 1 | 1 | 1 | |
| Meningeoma | 1 | 177 | 7444 | |

TABLE II-continued

Determination of the GnRH concentration
The results of the GnRH receptor determination using the radio receptor assay according to the invention of tissue samples of several patients are listed.

| | ER fmol/ mg prot | PgR Fmol/ mg prot | GnRH rec. atomol/ mg prot | Finding |
|---|---|---|---|---|
| Histological samples | 10 | 20 | 1000 | negative |
| | 10-20 | 20-30 | 1000-3000 | weakly positive |
| | 20 | 30 | 3000-5000 | positive |
| | 50 | 100 | 5000 | strongly positive |
| Meningeoma | 1 | 550 | 1588 | |
| GBM | 1 | 1 | 4466 | |
| Additional values: | | | | |
| Chordoma | 1 | 1 | 1117 | weakly positive |
| Intraspinal meningeoma | 3 | 7 | 1640 | weakly positive |
| Brain metastasis of plate epithelium carcinoma of the lung | 1 | 1 | 200 | negative |
| Normal brain tissue | 4 | 1 | 460 | negative |

ER = estrogen receptor,
PgR = progesterone receptor,
GnRH rec. = GnRH receptor

Example 14

Proliferation Assay Using the Human Malignant Melanoma Cell Line MV3

The human melanoma cell line MV3 was cultured (in long-term culture in RPMI medium (Gibco Co.) with 1% Penstrep and 10% of heat-inactivated fetal calf serum). The proliferation assay was carried out with 6×10$^2$ cells per well in 96 well plates. First, the cells were removed from the culture flask with a 0.02 mM solution and then washed in standard PBS solution. Following centrifugation for 10 minutes (1200 g) the supernatant was discarded and the pellet resuspended in 1 ml medium. An aliquot of 20 µl of the cells was diluted with trypan blue to obtain an 1:20 dilution. Trypan blue stains the necrotic cells. Then counting was performed in a Neubauer counting chamber. Evaluation was performed by daily determination of 4 values starting at day 0 and multiplying the mean values of the cell counts ×10$^4$ × dilution factor 20 to obtain the cell count. During 5 days, the measurement was performed 4 × daily in a Biomec spectrophotometer.

The method for determination of tumor cell proliferation is described in Lü, H. Q., et al., 1996, Journal of Cancer Research and Clinical Oncology, 122, 335-342.

The cell line was treated with (Gly-OH10)-LHRH, the LHRH hormone (FIG. 3) (Sigma Chemical Co., No. L8008) or Triptorelin, an LHRH agonist (FIG. 2) (Sigma Chemical Co., No. L9761) or Antide, a LHRH antagonist (FIG. 1) (Sigma Chemical Co., No. A8802).

In the concentrations of 10$^{-4}$ M, 10$^{-5}$ M, and 10$^{-66}$ M using medium as a negative control from day 4 on the following results were obtained:

Referring to FIG. 1: For Antide (GnRH antagonist) a clear inhibition of proliferation is seen in the high concentrations of 10$^{-4}$ M and 10$^{-5}$ M of 15% and 35%, respectively, (similar as described by Emons et al., 1993, supra, but with later onset as compared to the ovarian carcinoma cell lines used therein in which an anti-proliferative effect of the antagonists in one of the two cell lines occurred from day 1 on). At a concentration of $10^{-6}$ M no inhibition of the proliferation was observed but a stimulation of the growth of 40%. This paradox in vitro effect of GnRH antagonists is similar to that described in Limonta et al., 1993, J. Clin. Endocrinol. Metab., 76, 839-845, for prostate carcinomas with GnRH receptors. A similar in vitro effect for relatively low concentrations is also known for Tamoxifen in the MCF-7 mammary carcinoma cell line (Zänker, K., et al., 1995).

For Triptorelin (GnRH agonist) (see FIG. 2) an inhibition of the proliferation of 15% was observed from day 4 on at the concentrations mentioned. In Emons et al., 1993, supra, this has been observed already starting from day 1 for both ovarian carcinoma cell lines under a Triptorelin treatment of $10^{-5}$ M, and 40% inhibition was observed on day 6.

These findings indicate the presence of a direct anti-proliferative effect of Antide and Triptorelin on malignant melanoma. It has also been proven that GnRH receptors are present on the human malignant melanoma cell line MV 3 since binding of a non-ligand to the tumor cells can be excluded.

Figure 2:
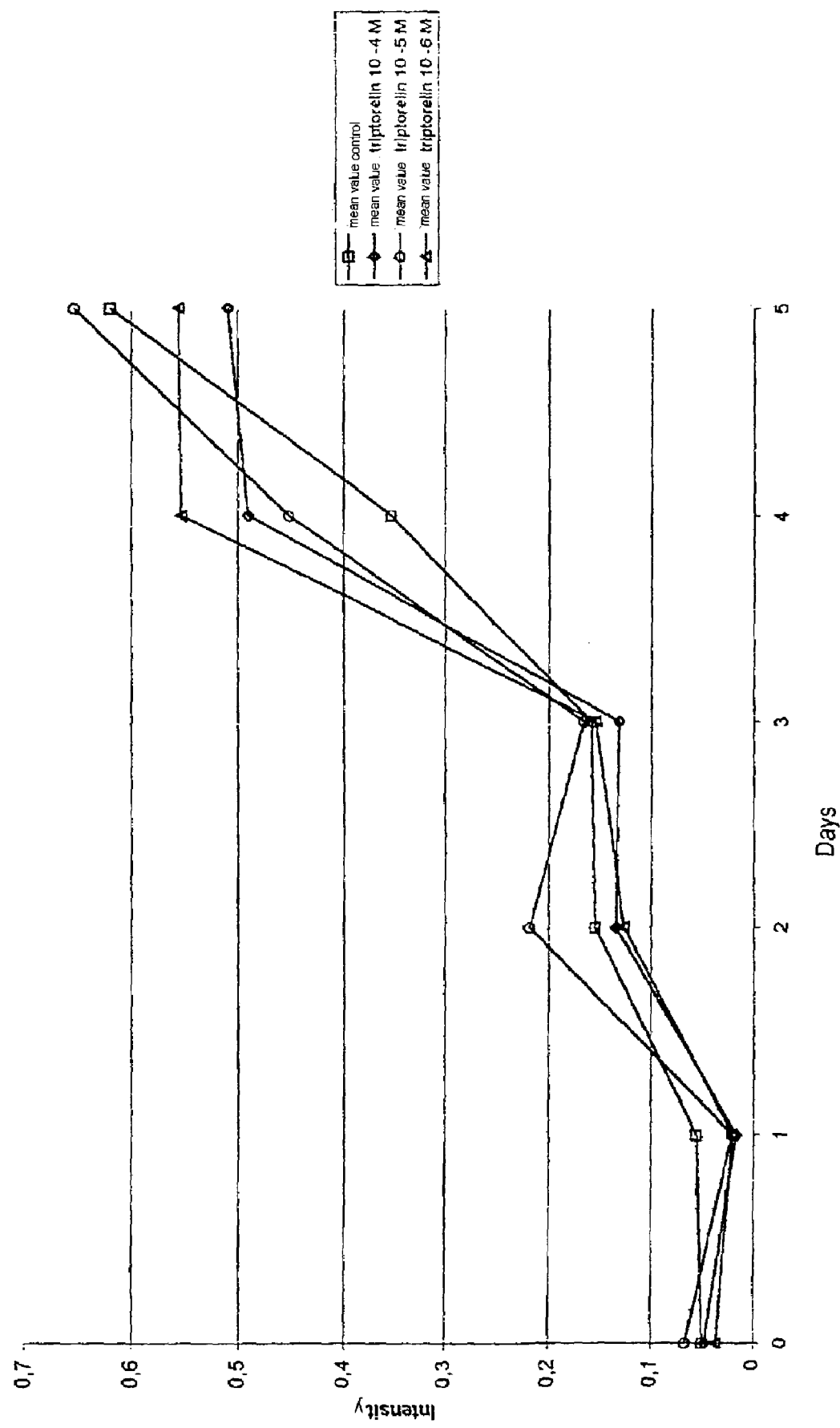
FIG. 2: Inhibition of proliferation on malignant melanoma MV3 cells by Triptorelin (GnRH agonist).
Figure 3:
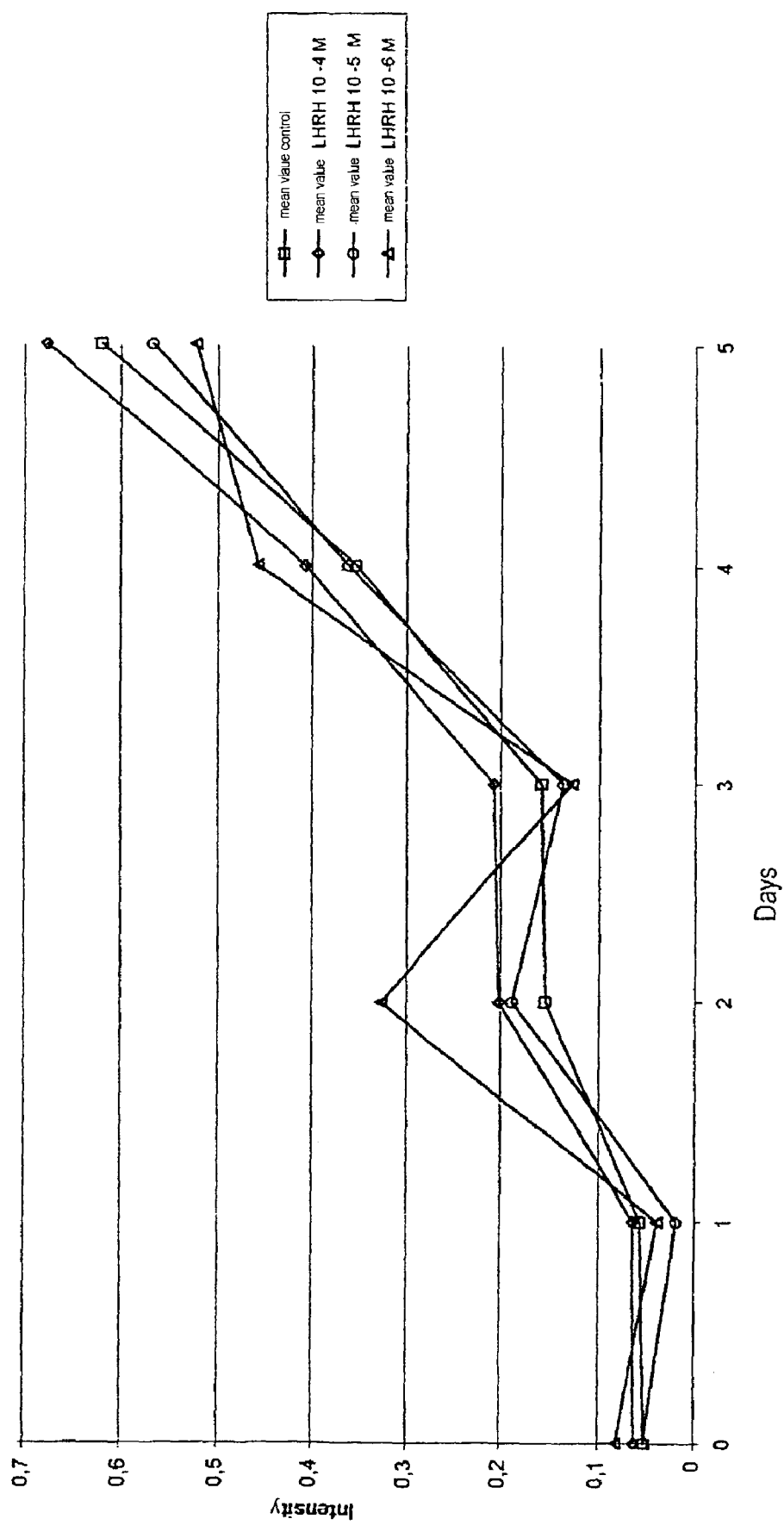
FIG. 3: Inhibition of proliferation on malignant melanoma MV3 cells by LHRH hormone.

The graphs of FIGS. 1-3 prove that malignant melanoma MV3 is LHRH hormone-dependent tumor.

Thus, also in vitro the LHRH hormone functions as a positive growth factor. The function of LHRH hormone produced in an autocrine manner is inhibited by Antide and Triptorelin.

Example 15

GnRH Agonist as an Inhibitor of Cell Proliferation and Invasive Growth of Melanoma Cells As another example, demonstrated by RT-PCR and by Western blot analysis that GnRH receptors are expressed in the highly proliferative and metastatic BLM melanoma cell line. Disclosed is a dose-dependent inhibition of cell proliferation after the treatment of BLM cells with a GnRH agonist. Shown is that the activation of the GnRH receptors also reduces the ability of melanoma cells to invade a reconstituted basement membrane Cell Proliferation Studies BLM cells were plated at a density of 700 cells/cm$^2$ in 10-mm dishes in culture medium. Cells were allowed to attach and start growing for 3 days; the seeding media were then changed. Cells were treated daily (the drug was added to the medium every day), for 7 days, with LHRH-A ($10^{-11}$-$10^{-6}$ M); the medium was changed at every two days. At the end of the treatment, cells were collected and counted by hemocytometer.

To confirm the specificity of the action of LHRH-A on melanoma cell proliferation, it was investigated whether the effects of the LHRH agonist might be counteracted by a potent GnRH antagonist. A preliminary experiment was performed to select the dose of the GnRH antagonist (ANT) to be used. To this purpose, BLM cells were treated daily with ANT at different doses ($10^{-11}$-$10^{-6}$ M). Cells were harvested and counted after 7 days of treatment. Subsequently, BLM cells were treated daily, for 7 days, with LHRH-A ($10^{-7}$ M), either in the absence or in the presence of ANT ($10^{-7}$ M). Cells were counted 7 days after the beginning of the treatment.

The antiproliferative action of GnRH agonists on melanoma cells is further investigated in another melanoma cell line (Me15392). These experiments have been carried out as described above for BLM cells (same GnRH agonist, same doses of the drug and same length of treatment, etc.).

All proliferation experiments were performed in four to six replicates. The data obtained from three independent experiments were analyzed according to the Dunnett's test after one-way ANOVA.

Matrigel Gel Assay

For invasion and migration experiments, the $10^{-6}$ M dose of LHRH-A has been chosen, since it was the most effective in earlier proliferation studies. This dose has been also used in previous papers analyzing the interaction between GnRH agonists and stimulatory growth factors in prostate cancer cells (25,26).

Subconfluent BLM cells were collected by trypsinization, resuspended in culture medium and seeded in 20 µL (150,000 cells/drop) on the lid of a culture dish. The lid was then placed on a dish filled with 2 mL of culture medium and incubated at 37 C for 48 h. Matrigel solution (80 µL, 2.7 mg/mL) was pipetted onto the bottom of wells of a 24-well culture dish, and left to set at 37 C. Cell aggregates were transferred over the cushion and then overlaid with additional 20 µL of Matrigel. The aggregates into Matrigel were covered with 400 µL culture medium in the absence or in the presence of LHRH-A ($10^{-6}$ M). The aggregates were then observed daily under a light microscope and at the end of the incubation time phase-contrast pictures of the aggregates were taken.

Chemomigration Assay

The assay was performed using a 48-well Boyden's chamber, according to the manufacturer's instruction (Neuroprobe, Cabin John, MD). Subconfluent BLM cells, grown in culture medium, were pretreated for 5 days with LHRH-A ($10^{-6}$ M) and harvested at the end of the treatment. BLM cell suspensions ($10^5$ cells/50 µL), resuspended in culture medium deprived of FBS, were placed in the open-bottom wells of the upper compartment of the chamber. Each pair of wells were separated by polyvinilpyrrolidone-free polycarbonate porous membrane (8-µm pores) pre-coated with gelatine (0.2 mg/mL in PBS). The chemoattractant (FBS 5%) was placed in the lower compartment of the chamber. The chamber was then kept for 4 h in the cell culture incubator. After that, the cells migrated through the pores, and adhered to the underside of the membrane, were fixed, stained (Diff-Quick kit, DADE, Dudingen, CH) and mounted onto glass slides. For quantitative analysis, six random objective fields of stained cells were counted for each well (8 wells/experimental group) and the mean number of migrating cells/mm$^2$ was calculated. The data obtained from four independent experiments were compared by ANOVA and Dunnett's test.

Results

Expression of GnRH and of the GnRH Receptor in BLM Melanoma Cells

Figure 4:
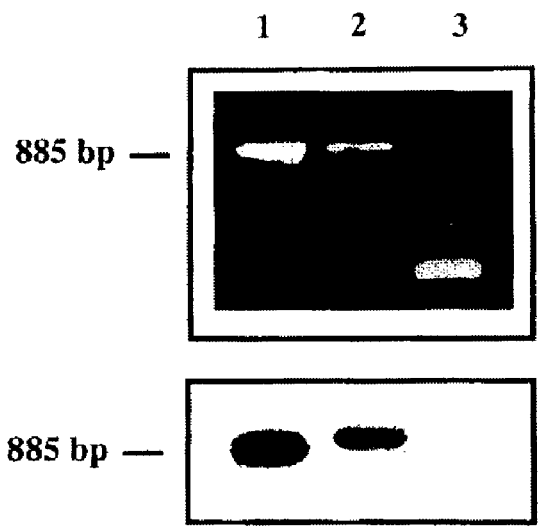
FIG. 4: RT-PCR analysis of the expression of GnRH in BLM cells. Top. Ethidium bromide-stained agarose gel of the amplified cDNAs. Bottom, Autoradiography of the Southern blot obtained from the gel shown in the top panel after hybridization with a 32P-labeled oligonucleotide GnRH cDNA probe. Lane 1, BLM cells; lane 2, prostate cancer cells; lane 3, TR-PCR control (308 bp). One of three experiments performed is reported.

The expression of GnRH and of GnRH receptor mRNA in melanoma BLM cells was investigated by RT-PCR. After PCR, the amplified cDNAs were electrophoresed on a 1.5% agarose gel containing ethidium bromide. With regard to the expression of GnRH, the predicted 228-bp fragment is observed in BLM cells (FIG. 4, upper panel, lane 1) as well as in prostate cancer cells used as controls (FIG. 4, upper panel, lane 2). No cDNA band is detected in samples without RT (data not shown), ruling out the possibility of genomic DNA contamination. After Southern blotting, the cDNA fragments obtained from BLM and prostate cancer cells, hybridizes with the $^{32}$P-labeled oligonucleotide probe specific for GnRH cDNA (FIG. 4, lower panel, lanes 1 and 2).

Figure 5:
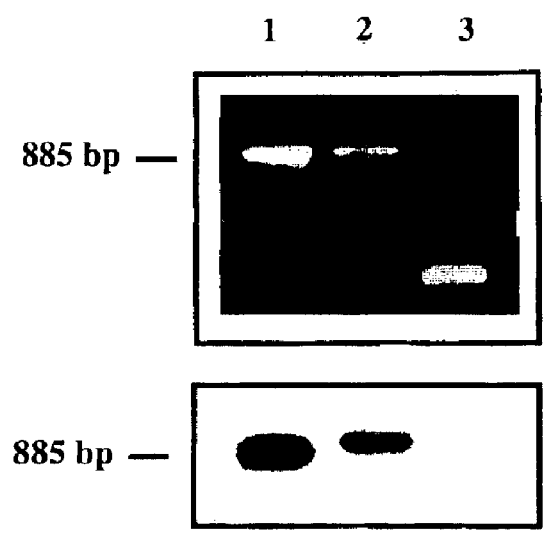
FIG. 5: RT-PCR analysis of the expression of GnRH receptor in BLM cells. Top. Ethidium bromide-stained agarose gel of the amplified cDNAs. Bottom, Autoradiography of the Southern blot obtained from the gel shown in the top panel after hybridization with a 32P-labeled oligonucleotide GnRHreceptor cDNA probe. Lane 1, BLM cells; lane 2, prostate cancer cells; lane 3, TR-PCR control (308 bp). One of three experiments performed is reported.

In the case of the expression of the GnRH receptor mRNA, the results obtained demonstrate that the predicted 885-bp cDNA fragment can be obtained in BLM (FIG. 5, upper panel, lane 1), as well as in prostate cancer cells (FIG. 5, upper panel, lane 2). No cDNA band is amplified in samples without RT (data not shown). As expected, the GnRH receptor cDNA bands hybridize with the specific $^{32}$P-labeled oligonucleotide probe specific for GnRH receptor cDNA (FIG. 5, lower panel, lanes 1 and 2).

Figure 6:
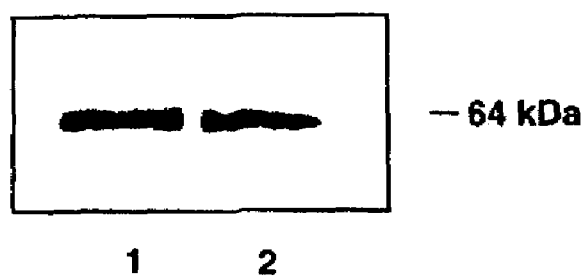
FIG. 6: Western blot analysis of solubilized membrane proteins from BLM cells (lane 1) and prostate cancer cells (lane 2), probed with the FIG. 4 monoclonal antibody raised against the human pituitary GnRH receptor. One experiment representative of three is reported.

The presence of GnRH receptors in melanoma cells has been further investigated at the protein level, by Western blotting technique, and by using the FIG. 4 monoclonal antibody specifically raised against the human pituitary GnRH receptor. As shown in FIG. 6, a major protein band of approximately 64 kDa molecular mass is identified by the antibody in BLM cells (lane 1) like in prostate cancer cells (FIG. 6, lane 2). This molecular weight corresponds to that previously reported for the human pituitary GnRH receptor. The level of expression of this receptor is not found to be affected by a 7-days treatment with the GnRH agonist (data not shown).

Effect of GnRH Agonists on the Proliferation of BLM Melanoma Cells

Figure 7:
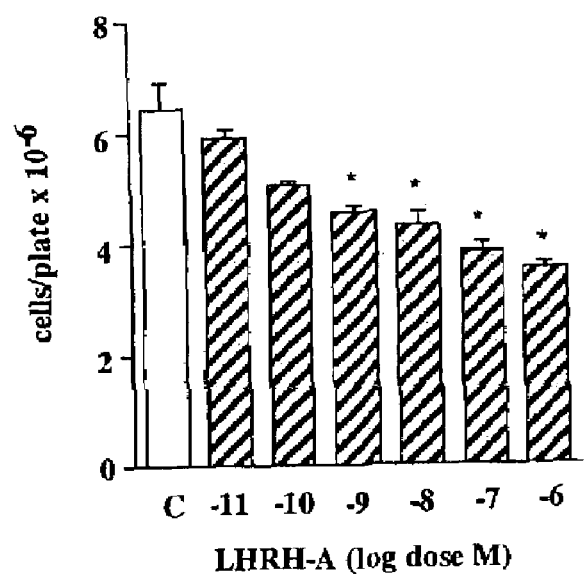
FIG. 7: Effects of the GnRH agonist (LHRH-A) on the proliferation of BLM cells. Results are expressed as mean cell number per plate ±SE. *, P<0.05 vs. controls (C).

The observation that both GnRH and GnRH receptors are expressed in BLM cells, prompted us to investigate whether this GnRH-based system might be involved in the local control of melanoma cell growth. To this purpose, BLM cells were treated daily, for 7 days, with the potent GnRH agonist LHRH-A ($10^{-11}$-$10^{-6}$ M). The treatment resulted in a significant and dose-dependent inhibition of cell proliferation (FIG. 7).

Figure 8A:
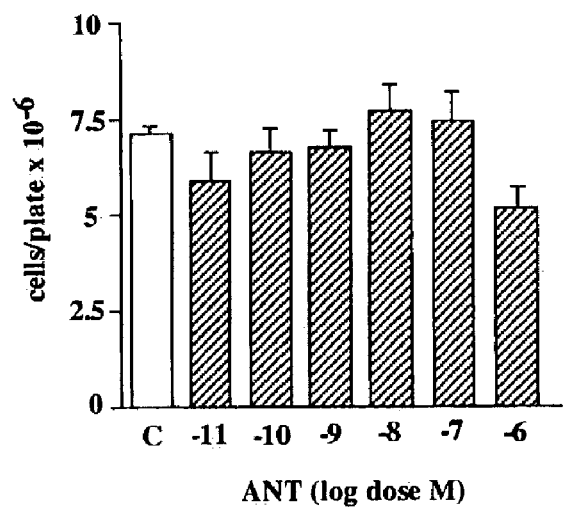
FIG. 8: A) Effects of the GnRH antagonist 9 ANT) on the proliferation of BLM cells. B) effects of the GnRH antagonist (ANT, $10^{-7}$M) on the inhibition of BLM cell proliferation induced by the GnRH agonist (LHRH-A, $10^{-7}$M). Results are expressed as mean cell number per plate ±SE. *, P<0.05 vs. controls (C).
Figure 8B:
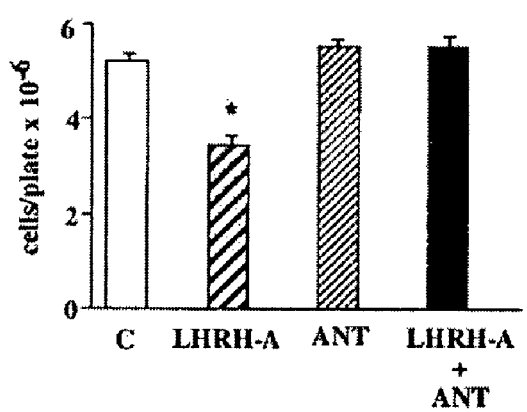

Further studies were performed to evaluate whether the antiproliferative action of LHRH-A on melanoma cells could be antagonized by the simultaneous treatment of the cells with the GnRH antagonist ANT. In preliminary experiments, the activity of ANT was evaluated. FIG. 8A shows that the antagonist does not affect the proliferation of the cells, when given at the doses $10^{-11}$–$10^{-7}$ M. The compound reduces slightly, but not significantly, the growth of BLM cells at the dose of $10^{-6}$ M. For subsequent experiments, the dose of $10^{-7}$ M was then selected. FIG. 8B confirms that ANT ($10^{-7}$ M), when given alone, has no effect on cell proliferation; on the other hand, ANT totally blocks the antiproliferative action exhibited by LHRH-A.

Expression and Role of GnRH Receptors in Me15392 Melanoma Cells

Figure 9:
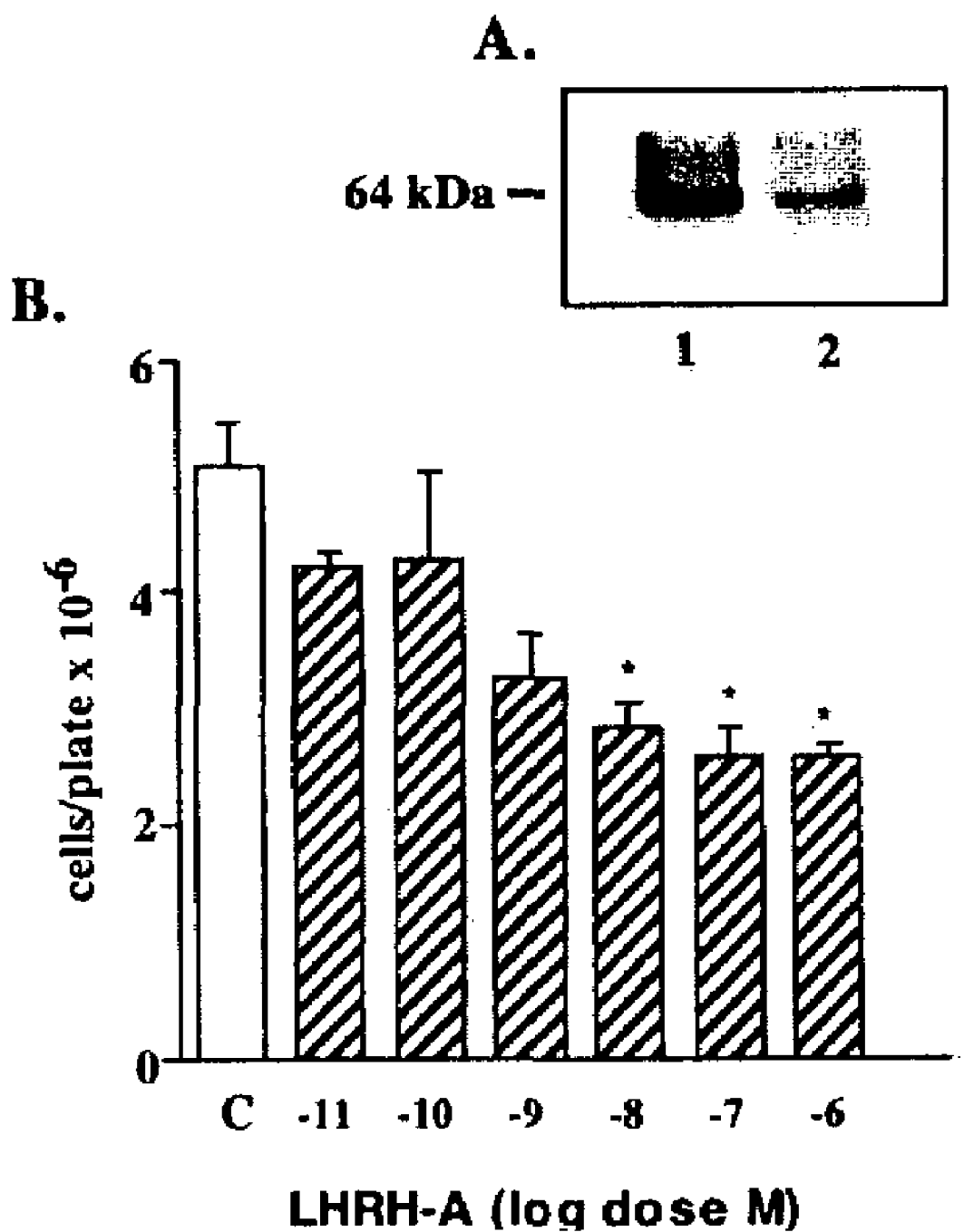
FIG. 9: A) Western blot analysis of the expression of the GnRH receptor in Me15392 cells. Lane 1, BLM cells; lane 2, ME15392 cells. B) Effect of the GnRH agonist (LHRH-A) on the proliferation of Me 15392 cells. Results are expressed as mean cell number per plate ±SE. *, P<0.05 vs. controls (C).

The presence of GnRH receptors, and their role in the control of melanoma cell proliferation have been further investigated in an additional melanoma cell line (Me15392). By Western blot analysis, and by using the FIG. 4 monoclonal antibody, we demonstrate that a protein band of 64 kDa is present in membrane preparations from Me15392 cells (FIG. 9A, lane 2). The molecular weight of this band corresponds to that found in BLM cells (FIG. 9A, lane 1).

Like in the case of BLM cells, the treatment of Me15392 cells with LHRH-A ($10^{-11}$-$10^{-6}$ M), for 7 days, results in a significant and dose-dependent inhibition of cell proliferation (FIG. 9B).

Binding Parameters of LHRH Receptors in BLM and Me15392 Melanoma Cells

GnRH receptors in melanoma cells have been analyzed also in terms of binding parameters. Binding sites for $^{125}$I-LHRH-A have been found to be present on the membranes of both BLM and Me15392 cells. Computer analysis of the data obtained from the displacement curves revealed the presence of a single class of high-affinity binding sites ($K_d$ in the nanomolar range) in both melanoma cell lines, as well as in rat pituitaries used as controls (Table III).

TABLE III

Characteristics of $^{125}$I-LHRH-A binding to human melenoma cell membranes

|  | Dissociation constant | $^{125}$I-LHRH-A binding Capacity (Fmoles/mg protein) |
|---|---|---|
| BLM cells | 0.7-1.1 nM | 150-200 |
| ME15392 cells | 0.1-0.6 nM | 200-250 |
| Rat pituitaries | 1.5-2.0 nM | 70-100 |

Binding characteristics were evaluated from displacement curves as described in Materials and Methods.

This observation agrees with previous data showing the expression of high-affinity GnRH receptors in tumors of the reproductive tract (28,29).

Effect of GnRH Agonists on the Metastatic Potential of BLM Melanoma Cells

Figure 10:
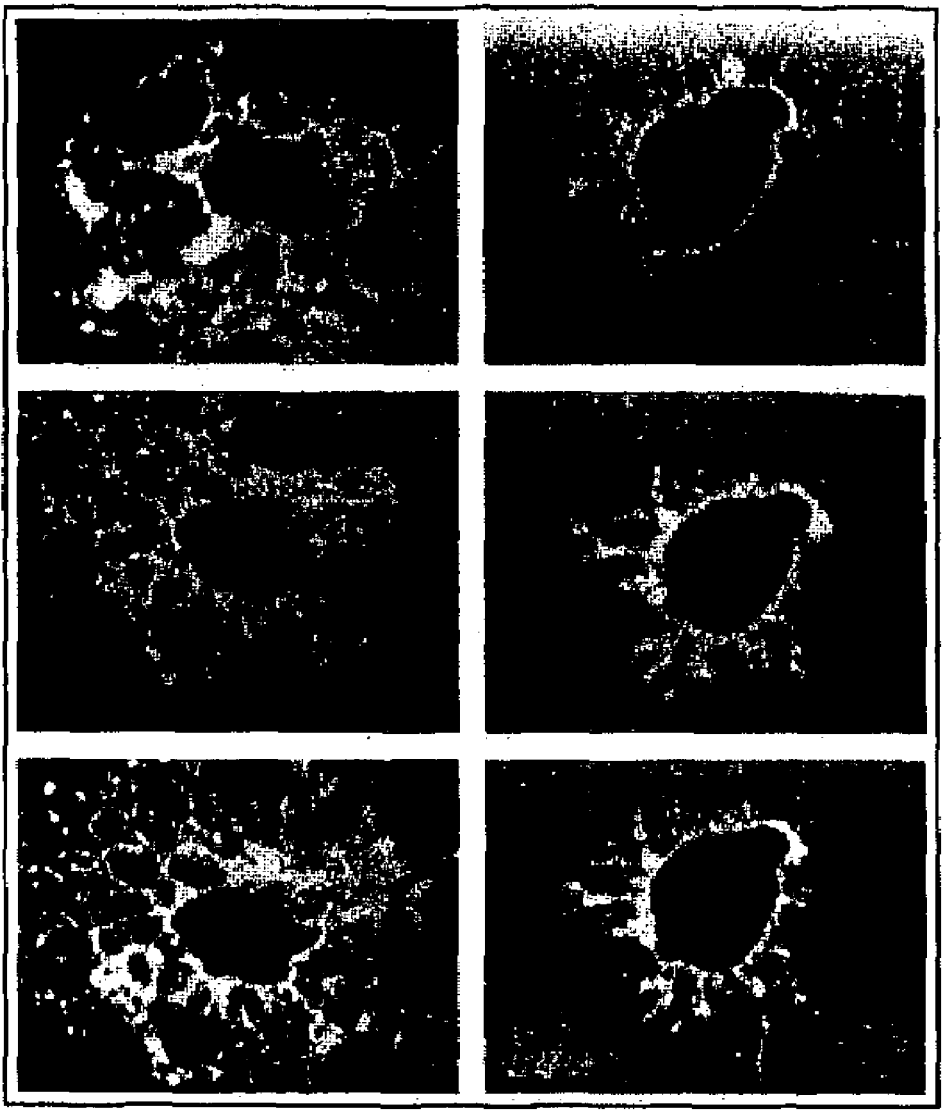
FIG. 10: Effects of the GnRH agonist (LHRH-A) on the capacity of BLM melanoma cells to invade a reconstituted basement membrane after 4, 8, and 12 days of treatment. Results from one of four experiments performed are reported. Scale bar 700 µm.

These experiments have been performed to verify whether the activation of locally expressed GnRH receptors might affect the metastatic potential of melanoma cells. First, we have studied the effects of the GnRH agonist LHRH-A ($10^{-6}$ M) on the ability of BLM cells to invade a matrix of a reconstituted basement membrane (Matrigel). BLM cells spontaneously form cell aggregates in Matrigel, when prepared by the hanging-drop technique. FIG. 10 shows that BLM cells actively leave the aggregate, and invade the Matrigel preparation at 4, 8 and 12 days. The treatment of BLM cells with ZOLADEX® completely abrogates the migration of the cells through the Matrigel, at all time intervals considered (FIG. 10).

Figure 11:
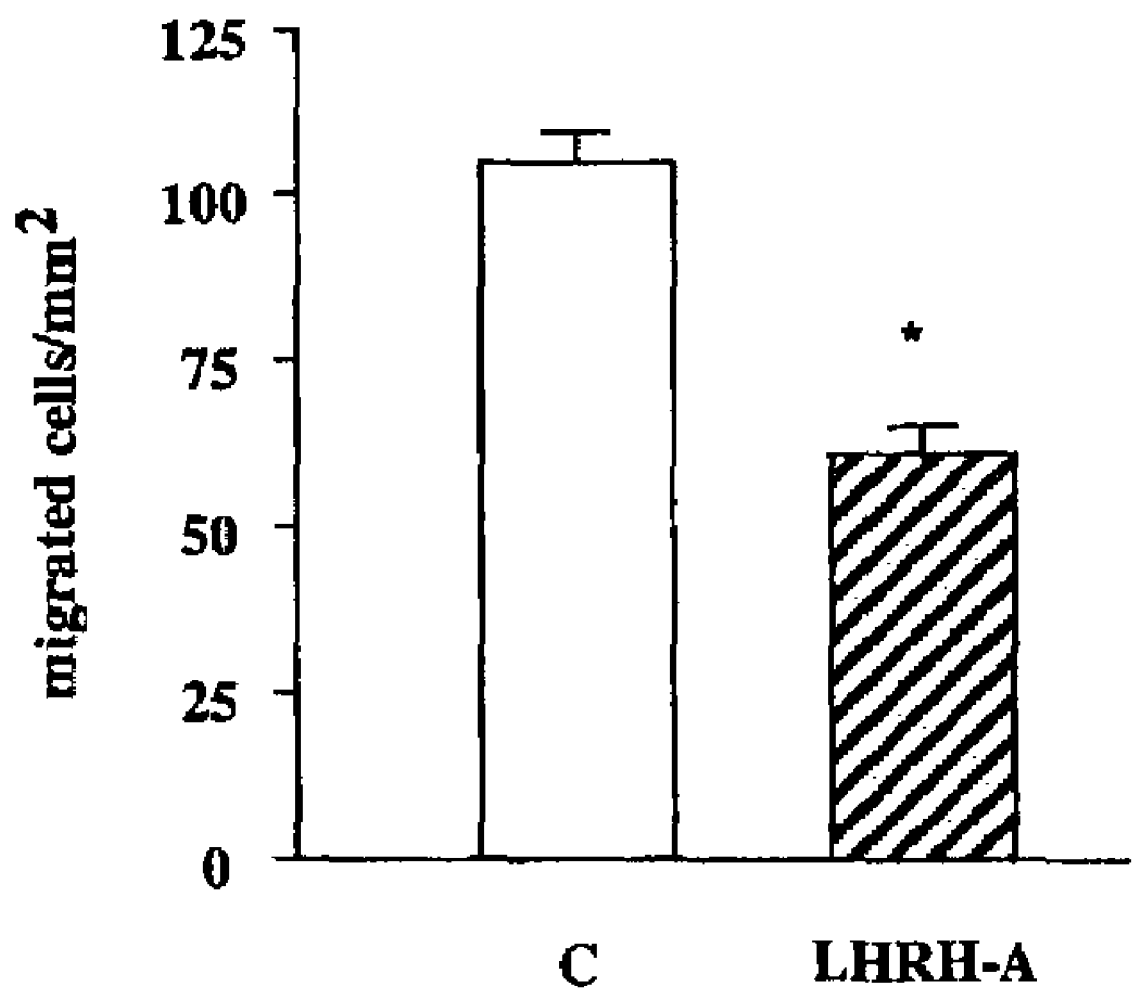
FIG. 11: Effects of the GnRH agonist (LHRH-A) on the ability of BLM melanoma cells to migrate toward a chemotactic stimulus (FBS 5%). P<0.05 vs. controls (C).

Analyzed then was whether GnRH agonists might affect the ability of melanoma cells to migrate towards a chemo attractant, using the Boyden's chamber technique and FBS 5% as the chemotactic stimulus. We have observed that, when BLM cells were pretreated with ZOLADEX® ($10^{-6}$ M) for 5 days, the number of the cells that migrate in response to the chemo attractant is significantly decreased when compared to control cells (FIG. 11).

Example 16

GnRH Agonist as an Inhibitor of Tumor Cell Proliferation: In vivo Study in Nude Mice Inoculated with Malignant Melanoma Low Dosage Experiment:

Materials and Methods:

Sixteen male nude mice were injected s.c. in the flank with $1 \times 10^6$ (0.2 ml/mouse) BLM cells. The treatment started the same day: Eight mice received daily 100 µg ZOLADEX® per mouse in 200 µl saline. Eight control mice were treated with 200 µl saline each. The treatment lasted 2-3 weeks. Every 2 to 3 days the volume of the tumors was determined by caliper.

Results:

BLM cells, when injected i.v. give rise to metastases, mainly in the heart. The BLM tumors grew faster in the controls. In ZOLADEX® treated mice, measured tumors were 15-20% smaller with respect to the controls.

The low-dosage results are comparable with standard melanoma chemotherapy (10% )(dacarbazie), showing that GnRH agonist can inhibit tumor growth in vivo. These are only first results. A second experiment will now be performed with a dosage of 200 micrograms per day.

Example 17

GnRH Agonists Inhibits the Growth of Glioblastoma Cells Expressing the GnRH Receptor The presence of GnRH binding sites on glioblastoma cells represents a diagnostic marker for nervous system tumors. Disclosed is the expression of GnRH receptors and their possible role in the control of high-grade glioma growth.

Materials and Methods

Chemicals

The GnRH agonist ZOLADEX® [D-Ser(tBu)$^6$Aza-Gly-LHRH] was kindly provided by AstraZeneca Pharmaceuticals, Divisione Farmaceutici (Milano, Italy).

Tumor Specimens

Glioblastoma biopsy specimens were either frozen at −80° C. or fixed with formalin and embedded in paraffin. Brain tissue was studied from a normal section specimen. Histological diagnoses were made according to the most recent WHO classification in 2000 from Kleihues, P. et al. (Kleihues P, Louis, D N, Scheithauer B W, Rorke L B, Reifenberger G, Burger P C, Cavenee W K. The WHO classification of tumors of the nervous system. J Neuropathol Exp Neurol 2002: 61: 215-25.)

Cell Cultures

The human glioblastoma U87 cell line, which possesses high proliferative activity, was kindly donated by Dr. Gaetano Finocchiaro (Instituto Neurologico 'Besta', Milano, Italy). Cells were routinely grown in RPMI medium (Seromed, Biochrom K G, Berlin, Germany), supplemented with 10% fetal bovine serum (FBS, Life Technologies, Paisley, Scotland), glutamine (1 mM) and antibiotics (100 UI/ml penicillin G sodium, 100 μg/ml streptomycin sulphate), in a humidified atmosphere of 5% $CO_2$ and 95% air. The human androgen-independent DU145 prostate cancer cell line was used as a positive control, since we have previously shown that a GnRH system is expressed in these cells. (Rambaldi A, Young D C, Griffin J D. Expression of the M-CSF (CSF-1) gene by human monocytes. Blood 1987; 69:1409-13.)

RT-PCR Analysis of GnRH Receptor mRNA

Total RNA from U87 cells, as well as from DU 145 cells and from human pituitary (Clontech, Palo Alto, Calif.) used as positive controls, was prepared according to a modification of the guanidinium thiocyanate/cesium chloride method. (Kakar S S, Grizzle W E, Neill J D. The nucleotide sequences of human GnRH receptors in breast and ovarian tumors are identical with that found in pituitary. Mol Cell Endocrinol 1994; 189:289-295.)

RNA (2 μg) was used in a reverse transcription reaction. cDNA synthesis was performed using the Gene AMP kit (Perkin Elmer Cetus, Norwalk, Conn.) with an oligo(dT)$_{16}$ primer for reverse transcriptase. Samples containing cDNAs were then amplified in a 100 μl solution containing PCR buffer (50 mM KCl, 10 mM Tris-HCl), 2 mM $MgCl_2$ and 2.5 U Taq polymerase. The amplification was carried out for 35 cycles (1-min denaturation at 94° C., 1-min primer annealing at 50° C., and 2-min primer extension at 72° C.) in the presence of the following primers: 5'-GCTTGAAGCTCTGTC-CTGGGA-3' (SEQ ID NO:1) (sense, −25 to −5, 30 pmol) and 5'-CCTAGGCATAGTAGGG-3' (SEQ ID NO:2) (antisense, 844-860, 30 pmol).[10] This pair of primers has been previously utilized in our laboratory to amplify GnRH receptor cDNA in prostate cancer cells.(Rambaldi A, Young D C, Griffin J D. Expression of the M-CSF (CSF-1) gene by human monocytes. Blood 1987; 69:1409-1413).

The predicted size of the amplified cDNA fragment was 885 bp. After PCR, the amplified cDNA products were separated on a 1.5% agarose gel and stained with ethidium bromide.

Western Blot Analysis of GnRH Receptor

Membrane fractions from U87MG and DU145 cells were prepared according to the protocol reported by Limonta et al. (Rambaldi A, Young D C, Griffin J D. Expression of the M-CSF (CSF-1) gene by human monocytes. Blood 1987; 69: 1409-1413.)

Samples were homogenized in 10 mM Tris-HCl (pH 7.6) buffer containing 1 mM dithiothreitol on ice. For tissue sample homogenization 50 mg tissue was cut into small pieces and homogenized in 250 μl buffer H [20 mM Tris/HCl (pH 8.0), 150 mM NaCl, 1 mM $CaCl_2$] using a Dounce glass homogenizator. The homogenates were centrifuged twice for 10 min each at 800×g to remove cellular debris, and the resulting supernatants were centrifuged at 18,000×g to pellet down the membrane fractions. The cell pellets were solubilized in RIPA buffer [50 mM Tris-HCl (pH 7.7), 150 mM NaCl, 0.8% Triton X-100, 0.8% sodium deoxycholate, 0.08% SDS, 10 mM ethylendiamine tetraacetate, 100 μM $Na_3VO_4$, 50 mM NaF, 0.3 mM phenylmethylsulfonylfluoride, and 5 mM iodoacetic acid] and electrophoresed on 10% polyacrylamide gel under reducing conditions. Equal amounts of tissue pellets were solubilized in 10 mM Tris/HCl pH 8.0 containing 0.1% Triton X-100, SDS-PAGE loading buffer was added, and samples were electrophoresed on SDS page-10% denaturing polyacrylamide gel under reducing conditions. Proteins were transferred onto a nitrocellulose filter, in 25 mM Tris-HCl (pH 8.3), 92 mM glycine and 20% methanol at 30 V overnight. Filters were probed with FIG. 4 mouse monoclonal antibody raised against the human pituitary GnRH receptor (kindly provided by Dr. A. A. Karande, Dept. of Biochemistry, Indian Institute of Science, Bangalore, India),[11] at a concentration of 5 μg/ml, followed by incubation with an antimouse IgG. Antibody bound to the GnRH receptor was detected with the ECL-Western blotting detection system after a 5 to 10 min exposure to a Hyperfilm-ECL X-ray film (Amersham, Milano, Italy), at room temperature. The specificity of FIG. 4 antibody for the human pituitary GnRH receptor has been previously demonstrated. (Rambaldi A, Young D C, Griffin J D. Expression of the M-CSF (CSF-1) gene by human monocytes. Blood 1987; 69:1409-1413. Dunnett C W. A multiple comparison procedure for comparing several treatments with a control. J Am Stat Assoc 1955; 50:1096-1121.)

Immunohistochemistry

Paraffin embedded, formalin fixed materials were examined for the immunohistochemical expression of GnRH receptor, including 10 glioblastomas, 6 fibrillary astrocytomas, 10 metastatic carcinomas, and various regions of a normal adult human brain. Sections were pretreated using microwaving in 1 mM EDTA buffer, pH 8.0, for 4×5 min. Mouse monoclonal anti-human LHRH receptor antibody, clone BM582 (DPC Biermann, Bad Nauheim, Germany) was used at a concentration of 0.1 μg/ml. Detection was performed with the Chem Mate Link Biotinylated Secondary Antibody system (Dako, Hamburg, Germany) and diaminobenzidine as chromogen using a Tech Mate Horizon automated staining apparatus.

Cell Proliferation Studies

U87MG cells were plated at a density of 1400 cells/$cm^2$ in 10-mm dishes in standard culture medium. Cells were allowed to attach and start growing for 3 days; the seeding media were then changed to experimental media. Cells were treated, for 7 days, with ZOLADEX® ($10^{-10}$-$10^{-6}$ M);

Medium was changed every two days. At the end of the treatment, cells were collected and counted by hemocytometer. Data obtained from three independent experiments were analyzed according to the Dunnett's test after one-way ANOVA. (Wormald P J, Eidne K A, Millar R P. Gonadotropin-releasing hormone receptors in human pituitary: ligand structural requirements, molecular size, and cationic effects. J Clin Endocrinol Metab 1985; 61:1190-1194.)

Results

Expression of GnRH Receptors in Cultured Glioblastoma Cells and in Glioblastoma Tissue First, we have verified expression of GnRH receptor mRNA in U87MG cells, since by RT-PCR specific transcripts were detected (FIG. 12A, lane 1). The size of the amplified cDNA corresponded to that found in human prostate cancer cells (FIG. 12A, lane 2) and in human pituitary (FIG. 12A, lane 3) (Clontech, Palo Alto, USA) utilized as positive controls. (Rambaldi A, Young D C, Griffin J D. Expression of the M-CSF (CSF-1) gene by human monocytes. Blood 1987; 69:1409-1413.)

The presence of GnRH receptors in glioblastoma cells was then demonstrated at the protein level. By Western blotting technique a band of approximately 64 kDa was identified in U87MG cell membrane preparations (FIG. 12B, lane 1). A band of the same size was also detected in membrane preparations from human prostate cancer cells, used as positive controls (FIG. 12B, lane 2). The molecular size of these bands corresponds to that reported for the human pituitary GnRH receptor. (Crawford E D, De Antonio E P, Labrie F, Schroder F H, Geller J. Endocrine therapy of prostatic cancer: optimal form and appropriate timing. J Clin Endocrinol Metab 1995; 80:1062-1078.)

Figure 13:
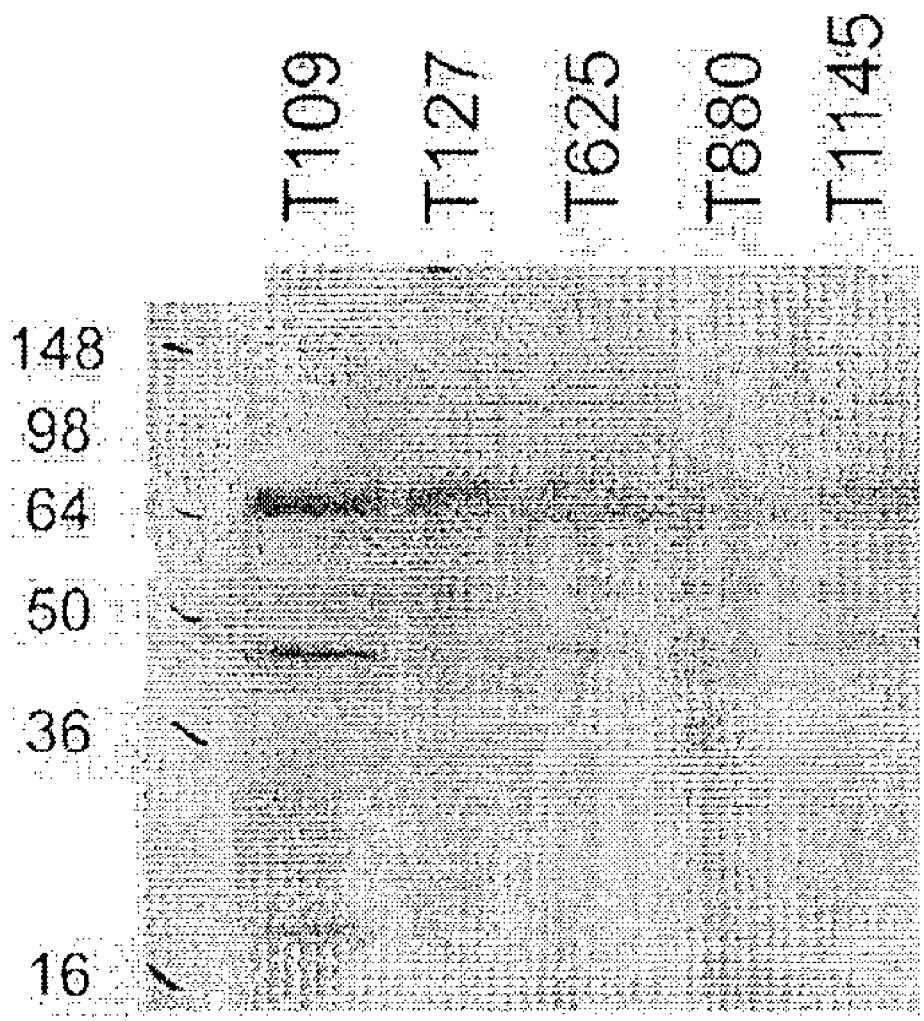
FIG. 13: Western blot of membrane fractions from five glioblastomas, termed T109, T127, T625, T880, and T 1145. All five glioblastomas show clearly visible bands at a size of approximately 64 kD.
Figure 14A:
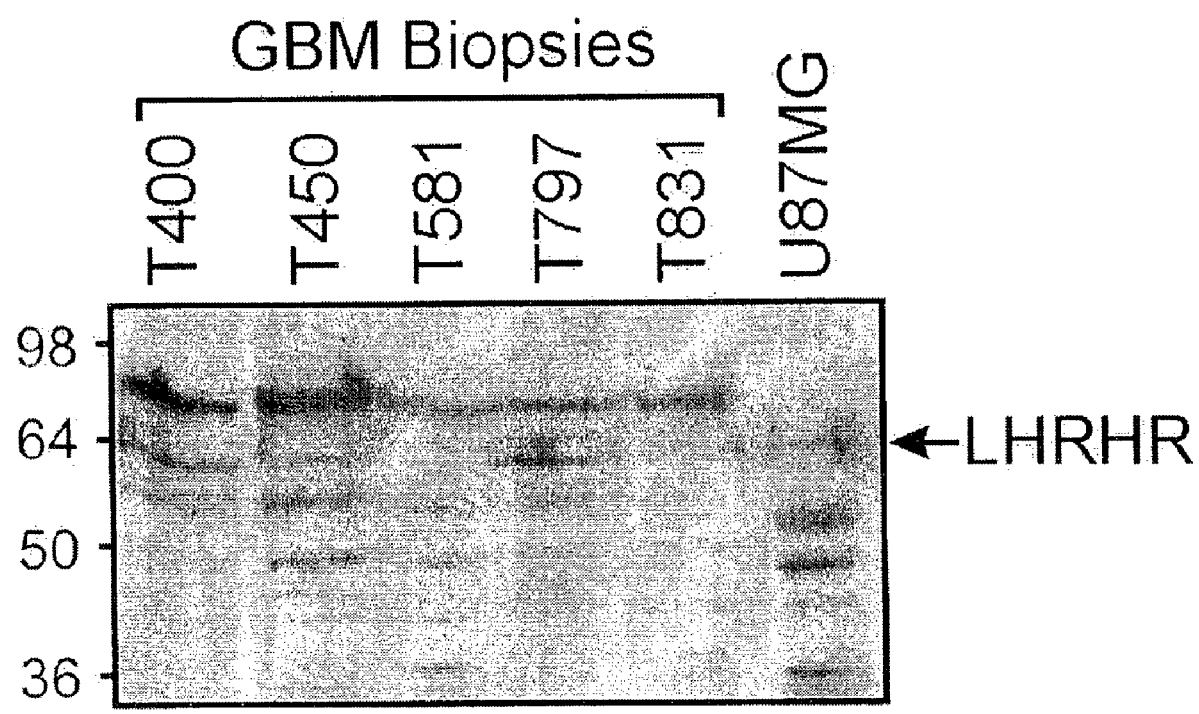
FIG. 14: Western blot of membrane fractions from five glioblastoma biopsies, termed T400, T450, T581, T797, and T831. All five glioblastoma biopsies show clearly visible bands of LHRH receptor at a size of approximately 64 kD. In A) U 87 MG glioblastoma cell line was used as a control. In B) The same five glioblastoma biopsies were tested in Western blot. U373MG glioblastoma cell line was used as a control.
Figure 14B:
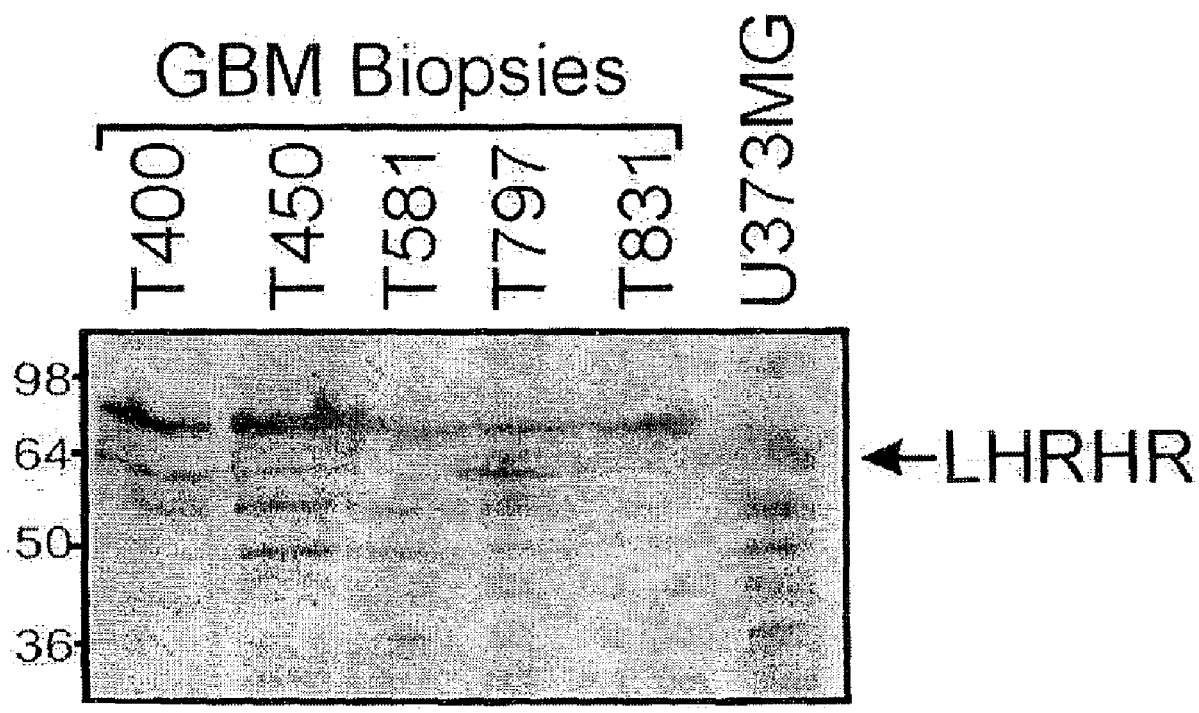

Western blotting reveals GnRH receptor in all five glioblastomas analyzed FIG. 13). And in 5 biopsies of glioblastomas (FIG. 14). The membrane fractions of the tumors shows distinct bands at approximately 64 kD.

Figure 15:
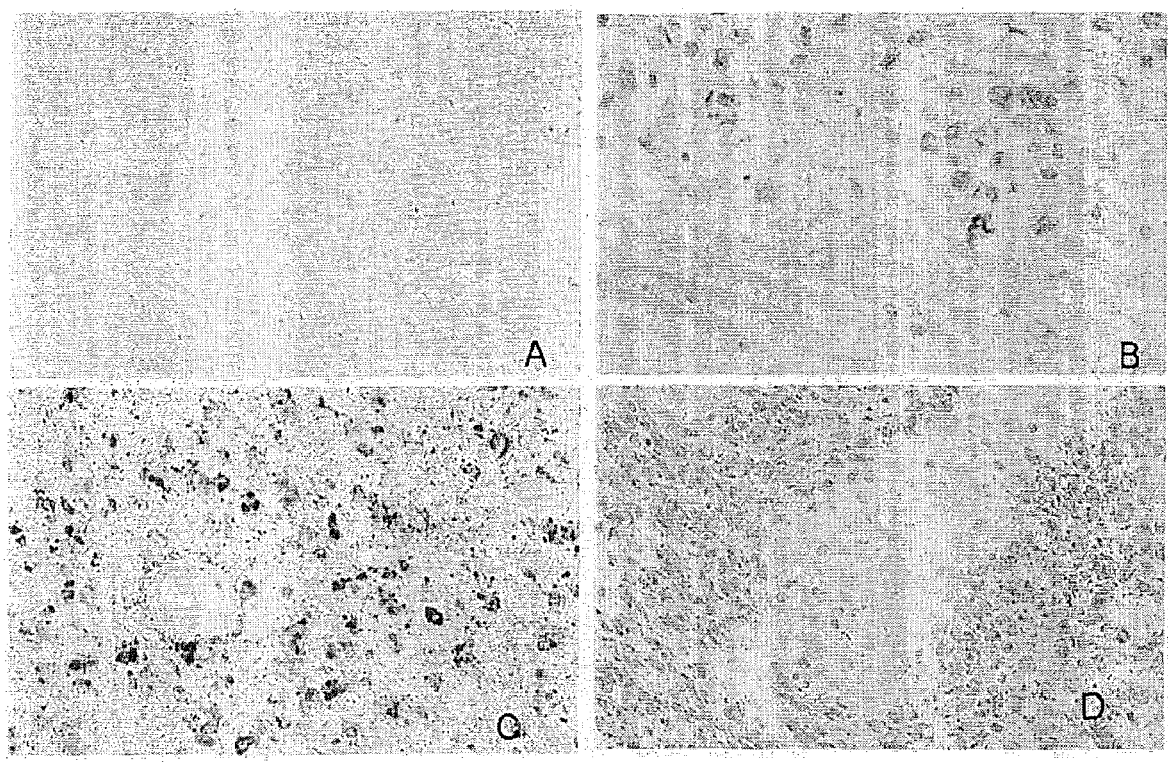
FIG. 15: Immunohistochemical staining for GnRH (LHRH) receptor. A) Weak positivity is seen in scattered neurons of the normal cerebral cortex (right). B) Reactive astrocytes (bottom) around metastatic carcinoma (top) exhibit faint immunoreactivity at cell membrane. C) Marked immunostaining is present in tumor cells but not in vascular cells (center) of fibrillary astrocytoma. D) glioblastoma exhibits marked staining for GnRH receptor, whereas hyperplastic vessel (center) is negative.

By using immunohistochemistry, all astrocytomas and glioblastomas strongly express GnRH receptor (FIG. 15). Most tumor cells exhibit a punctate staining pattern, while a few tumor cells show diffuse cytoplasmic staining. Blood vessels are negative, including the abnormal vascular proliferations typical of glioblastomas. In the normal adult brain, most intense staining is seen in scattered cells of the adenohypophysis. In the cerebral cortex, a few neurons and perivascular astrocytes weakly express GnRH receptor. A higher number of positive neurons is observed in hippocampus and cerebellum, while no immunoreactivity is seen in white matter and basal ganglia. Choroid plexus epithelial cells are strongly stained, but ependymal cells are negative. Interestingly, most reactive astrocytes show upregulation of GnRH receptor at the cell membrane, as demonstrated in brain tissue surrounding metastatic carcinomas. Staining of reactive astrocytes is distinct but generally weaker than that of neoplastic astrocytes.

Effect of a GnRH Agonist on Glioblastoma Cell Proliferation

The observation that GnRH receptors are expressed in U87 cells, both at mRNA and protein levels, prompted us to investigate the role of these receptors in the regulation of glioblastoma cell proliferation. Treatment of U87 cells with a potent GnRH agonist (ZOLADEX®) results in a significant decrease of the proliferation rate, ZOLADEX® being significantly effective at doses ranging from $10^{-8}$ to $10^{-6}$ M (FIG. 12C). The ZOLADEX®concentration of $10^{-8}$ M causes about 23% inhibition versus controls; ZOLADEX® concentration of $10^{-6}$ M causes about 45% inhibition versus controls. The anti-proliferative effect of ZOLADEX® on U87 is comparable to that previously observed in 1994 on prostate cancer cells DU145 by Dondi et al., Cancer Res, 1994; 54: 4091-4095.

The data reported here demonstrate that GnRH receptors are expressed in glioblastoma U87MG cells and in glioblastoma tumor specimens and that their activation by means of a potent GnRH agonist brings about a dose-dependent decrease of cell proliferation. The presence of GnRH receptors negatively involved in the control of cancer cell proliferation has already been reported (Emons G, Muller V, Ortmann O, Schulz K-D. Effects of LHRH analogues on mitogenic signal transduction in cancer cells. J Steroid Biochem Molec Biol 1998; 65:199-206; Imai A, Tamaya T. GnRH receptor and apoptotic signaling. Vit Horm 2000; 59:1-33.; Rambaldi A, Young D C, Griffin J D. Expression of the M-CSF (CSF-1) gene by human monocytes. Blood 1987; 69:1409-1413).

However, these functional studies have been performed on epithelial tumors, such as prostate, breast, ovarian and endometrial cancer. (Dondi et al, Cancer Res, 1994; 54: 4091-4095.; Emons G, Muller V, Ortmann O, Schulz K-D. Effects of LHRH analogues on mitogenic signal transduction in cancer cells. J Steroid Biochem Molec Biol 1998; 65:199-206; Imai A, Tamaya T. GnRH receptor and apoptotic signaling. Vit Horm 2000; 59:1-33.; Rambaldi A, Young D C, Griffin J D. Expression of the M-CSF (CSF-1) gene by human monocytes. Blood 1987; 69:1409-1413) GnRH agonists are widely and successfully used for the treatment of hormone-related cancers, mainly based on their ability to suppress the activity of the pituitary-gonadal axis. (Crawford E D, De Antonio E P, Labrie F, Schroder F H, Geller J. Endocrine therapy of prostatic cancer: optimal form and appropriate timing. J Clin Endocrinol Metab 1995; 80:1062-1078. Manni A. Hornonal approaches to the chemoprevention of endocrine-dependent tumors. Endocr-Rel Cancer 1999; 6:483-485).

The observation that these compounds exert an additional, more direct antiproliferative effect at the level of the tumor gives further support to the utility of GnRH analogues for the treatment of these neoplasms. This study represents the first report of an inhibitory activity of GnRH agonists on in vitro proliferation of glioblastoma cells expressing the GnRH receptor. Our finding of GnRH receptor up-regulation in tumor cells as compared to non-neoplastic astrocytes supports our hypothesis that the presence of GnRH receptors can be considered as a diagnostically useful marker in giomas. The data also disclose that GnRH receptors represent a molecular target for a favorable hormonal therapeutical approach, based on GnRH agonists.

The invention claimed is:

1. A method for decreasing cellular replication of ectodermally-derived, GnRH-receptor positive tumor cells in a subject, comprising:
   positively detecting and/or determining the presence of GnRH receptors and/or GnRH receptor concentration in the tumor cells, wherein the tumor cells are selected from the group consisting of lung- or neurally-derived oat-cell carcinoma cells and Kaposi sarcoma cells; and
   administering to said subject, a replication-decreasing amount of LHRH or a GnRH agonist selected from the group consisting of leuprorelin, triptorelin, buserelin, goserelin, nafarelin, and a pharmacologically acceptable salt of any thereof, which interacts with the GnRH receptor to thereby decrease the cellular replication of the oat-cell carcinoma cells or Kaposi sarcoma cells.

2. The method according to claim 1, wherein the LHRH or the GnRH agonist is used in combination with a cytotoxic substance.

3. The method according to claim 2, wherein the cytotoxic substance is coupled with the LHRH or the GnRH agonist.

4. A method for decreasing cellular replication of ectodermally-derived, GnRH-receptor positive tumor cells in a subject, comprising:
   positively detecting and/or determining the presence of GnRH receptors and/or GnRH receptor concentration in the tumor cells, wherein the tumor cells are selected from the group consisting of the malignant glioma cells or malignant melanoma cells; and
   administering to said subject, a replication-decreasing amount of a GnRH agonist selected from the group consisting of leuprorelin, triptorelin, buserelin, goserelin, nafarelin, and a pharmacologically acceptable salt of any thereof, which interacts with the GnRH receptor to thereby decrease the cellular replication of the malignant glioma cells or malignant melanoma cells.

5. The method according to claim 4, wherein said GnRH agonist is used in combination with a cytotoxic substance.

6. The method according to claim 5, wherein the cytotoxic substance is coupled with the GnRH agonist.

\* \* \* \* \*

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
```

```
<223> OTHER INFORMATION: synthesized sequence, primer for polymerase
      chain reaction

<400> SEQUENCE: 1
gcttgaagct ctgtcctggg a                                              21

<210> SEQ ID NO 2
<211> LENGTH: 17
<212> TYPE: DNA
<213> ORGANISM: Artificial sequence
<220> FEATURE:
<223> OTHER INFORMATION: synthesized sequence, primer for polymerase
      chain reaction

<400> SEQUENCE: 2
cctaggacat agtaggg                                                   17
```